United States Patent [19]

Santel et al.

[11] Patent Number: 5,585,384
[45] Date of Patent: Dec. 17, 1996

[54] SUBSTITUTED BICYCLIC 3-ARYL-PYRROLIDINE-2,4-DIONE DERIVATIVES

[75] Inventors: Hans J. Santel, Leverkusen; Robert R. Schmidt, Bergisch Gladbach; Ulrike Wachendorff-Neumann, Monheim; Christoph Erdelen, Leichlingen; Thomas Bretschneider, Siegburg; Reiner Fischer, Monheim; Hermann Hagemann, Leverkusen; Bernd-Wieland Krüger; Klaus Lürssen, both of Bergisch Gladbach, all of Germany

[73] Assignee: Bayer Aktiengesellschaft, Leverkusen, Germany

[21] Appl. No.: 292,111

[22] Filed: Aug. 17, 1994

Related U.S. Application Data

[60] Continuation-in-part of Ser. No. 134,430, Oct. 8, 1993, abandoned, which is a division of Ser. No. 826,303, Jan. 24, 1992, Pat. No. 5,288,874.

[30] Foreign Application Priority Data

Jan. 31, 1991 [DE] Germany .......................... 41 02 778.7

[51] Int. Cl.$^6$ .................. C07D 471/04; A01N 43/40; A01N 43/54

[52] U.S. Cl. .................. 514/299; 504/239; 514/269; 546/121

[58] Field of Search .................. 548/543; 546/121; 514/299, 269; 504/246, 239; 544/333

Primary Examiner—David B. Springer
Attorney, Agent, or Firm—Sprung Horn Kramer & Woods

[57] ABSTRACT

There have been discovered new bicyclic pyrrolidone compounds such as:

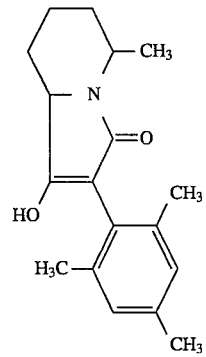

which are useful as insecticides, ascaricides and herbicides.

9 Claims, No Drawings

SUBSTITUTED BICYCLIC 3-ARYL-PYRROLIDINE-2,4-DIONE DERIVATIVES

This application is a continuation-in-part of application Ser. No. 08/134,430, filed on Oct. 8, 1993, now abandoned, which in turn is a divisional of application Ser. No. 07/826,303, filed on Jan. 24, 1992, now U.S. Pat. No. 5,288,874.

The invention relates to new bicyclic 3-aryl-pyrrolidine-2,4-dione derivatives, to a plurality of processes for their preparation, and to their use as pesticides (in particular as insecticides and acaricides) and as herbicides.

Pharmaceutical properties of 3-acyl-pyrrolidine-2,4-diones have previously been described (see S. Suzuki et al. Chem. Pharm. Bull. 15 1120 (1967)). Furthermore, N-phenylpyrrolidine-2,4-diones were synthesised by R. Schmierer and H. Mildenberger Liebigs Ann. Chem. 1985 1095. A biological activity of these compounds has not been described.

EP-A 0,262,399 discloses compounds of a similar structure (3-aryl-pyrrolidine-2,4-diones), of which, however, no herbicidal, insecticidal or acaricidal action is known. Other known substances are unsubstituted, bicyclic 3-aryl-pyrrolidine-2,4-dione derivatives (EP-A 355,599) and substituted monocyclic 3-aryl-pyrrolidine-2,4-dione derivatives (EP-A 377,893).

There have now been found new substituted bicyclic 3-aryl-pyrrolidine-2,4-dione derivatives of the formula (I)

in which

A and Q together represent an alkanediyl, alkenediyl, alkenedienyl or alkenetrienyl group having 3 to 6 carbon atoms, each of these groups being mono-substituted to polysubstituted by identical or different substituents each of these groups being substituted by halogen, hydroxyl, mercapto, in each case optionally substituted alkyl, alkoxy, alkylcarbonyloxy, alkylthio, cycloalkyl or aryl, and each of these groups additionally being interrupted, if appropriate, by one of the groups below B represents hydrogen or alkyl,
X represents alkyl, halogen or alkoxy,
Y represents hydrogen, alkyl, halogen, alkoxy or halogenoalkyl,
Z represents alkyl, halogen or alkoxy,
n represents a number 0, 1, 2 or 3,
represents hydrogen (a) or the groups —CO—R¹, (b)

(c)

—SO₂—R³, (d)

(e)

or

E (f)

in which

E represents a metal ion equivalent or an ammonium ion,

L and M represent oxygen and/or sulphur,

R¹ represents alkyl, alkenyl, alkoxyalkyl, alkylthioalkyl, polyalkoxyalkyl or cycloalkyl, each of which is optionally substituted by halogen and each of which can be interrupted by hetero atoms, or represents optionally substituted phenyl, optionally substituted phenylalkyl, substituted hetaryl, substituted phenoxyalkyl or substituted hetaryloxyalkyl and R² represents alkyl, alkenyl, alkoxyalkyl or polyalkoxyalkyl, each of which is optionally substituted by halogen, or represents optionally substituted phenyl or benzyl, R³, R⁴ and R⁵ independently of one another represent alkyl, alkoxy, alkylamino, dialkylamino, alkylthio, alkenylthio, alkinylthio and cycloalkylthio, each of which is optionally substituted by halogen, or represent optionally substituted phenyl, phenoxy or phenylthio, R⁶ and R⁷ independently of one another represent hydrogen, or alkyl, alkenyl, alkoxy or alkoxyalkyl, each of which is optionally substituted by halogen, or represent optionally substituted phenyl, or optionally substituted benzyl, R⁸ and R⁹ independently of one another represent hydrogen or alkyl, or R⁸ and R⁹ together represent an alkanediyl radical.

Taking into consideration the various meanings (a), (b), (c), (d), (e) and (f) of the group G of the general formula (I), the following main structures (Ia) to (If) result:

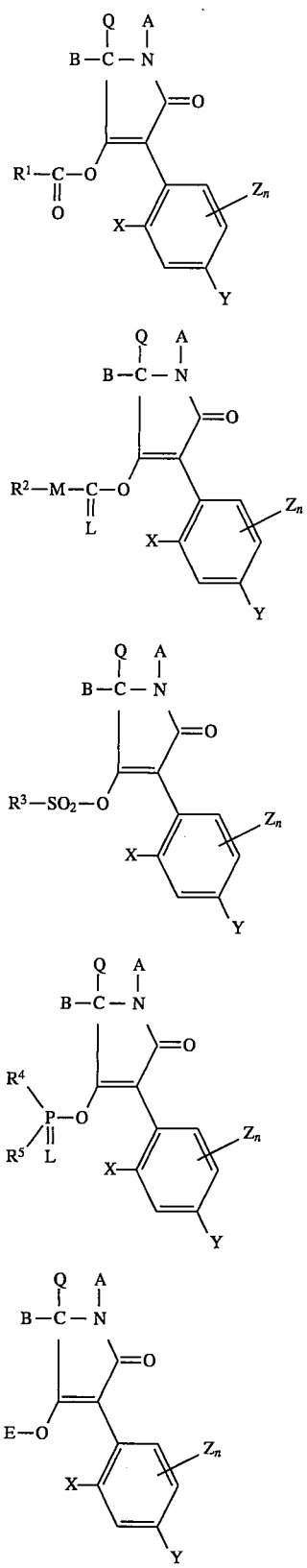

in which

A, B, Q, E, L, M, X, Y, $Z_n$, $R^1$, $R^2$, $R^3$, $R^4$, $R^5$, $R^6$ and $R^7$ have the abovementioned meanings.

Because of one or more chiral centres, the compounds of the formula (Ia)–(If) are generally obtained as a mixture of stereoisomers. They can be used both in the form of their mixtures of diastereomers and as pure diastereomers or enantiomers.

Furthermore, it has been found that the new substituted bicyclic 3-aryl-pyrrolidine-2,4-dione derivatives of the formula (I) are obtained by one of the processes described below.

(A-α) 3-Aryl-pyrrolidine-2,4-diones or enols thereof of the formula (Ia)

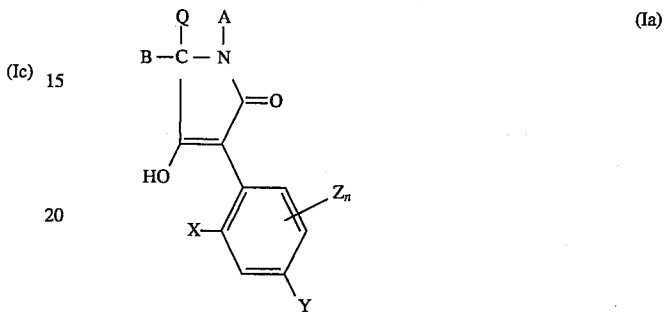

in which

A, B, Q, X, y, Z and n have the abovementioned meaning are obtained when

N-acyl amino acid esters of the formula (II)

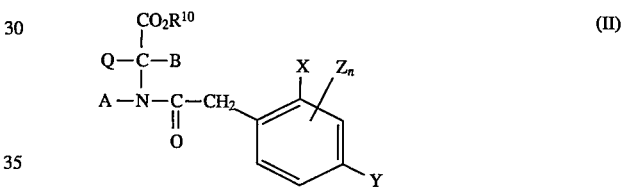

in which

A, B, Q, X, Y, Z and n have the abovementioned meaning and $R^{10}$ represents alkyl, are subjected to an intramolecular condensation reaction in the presence of a diluent and in the presence of a base: of β) compounds of the formula (Ia-a) obtained by process (Aα)

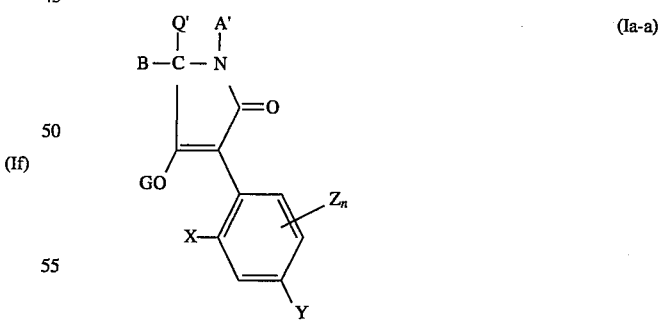

in which

B, X, Y, Z, n and G have the meanings given above and in which

A' and Q' together are standing for an alkanediyl-, alkenediyl-, alkenedienyl- or alkenetrienyl-residue each of which is substituted by hydroxy, are either transformed into esters of ethers by generally known methods or the hydroxy group is transformed in a first step in the corresponding ketones with the aid of oxydation methods like for example the Swern-oxidation or the Pfitzer-Moffart oxidation and then ketones are further reacted in a second step with amines, alcohols, diols, mercaptanes or dithiols, (B) compounds of the formula (Ib)

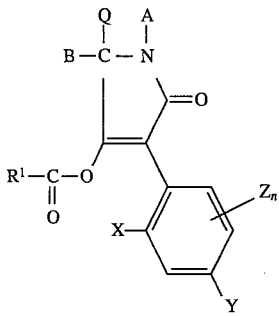

(Ib)

in which

A, B, Q, X, Y, Z, $R^1$ and n have the abovementioned meaning are obtained when compounds of the formula (Ia)

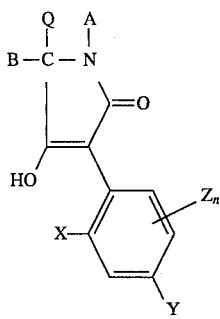

(Ia)

in which

A, B, Q, X, Y, Z and n have the abovementioned meaning
α) are reacted with acid halides of the general formula (III)

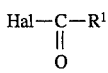

(III)

in which $R^1$ has the abovementioned meaning and

Hal represents halogen, in particular chlorine and bromine, if appropriate in the presence of a diluent and if appropriate in the presence of an acid-binding agent or β) are reacted with carboxylic anhydrides of the general formula (IV)

 (IV)

in which $R^1$ has the abovementioned meaning, if appropriate in the presence of a diluent and if appropriate in the presence of an acid-binding agent, or (C) compounds of the formula (Ic-1)

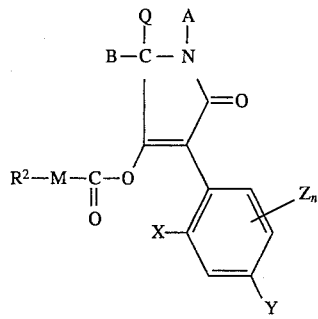

(Ic-1)

in which

A, B, Q, X, Y, Z, $R^2$ and n have the abovementioned meaning and

M represents oxygen or sulphur are obtained when compounds of the formula (Ia)

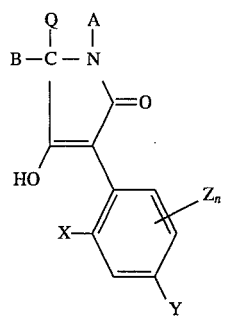

(Ia)

in which

A, B, Q, X, Y, Z and n have the abovementioned meaning are reacted with chloroformic ester or chloroformic thioester of the general formula (V)

 (V)

in which $R^2$ and M have the abovementioned meaning, if appropriate in the presence of a diluent and if appropriate in the presence of an acid-binding agent;

or (D) compounds of the formula (Ic-2)

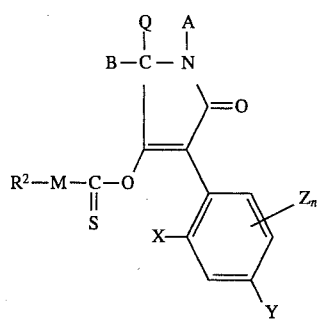

(Ic-2)

in which

A, B, Q, $R^2$, X, Y, Z and n have the abovementioned meaning and

M represents oxygen or sulphur are obtained when compounds of the formula (Ia)

(Ia)

[structure with Q, A, B—C—N, =O, HO, X, Y, Z_n]

in which

A, B, Q, X, Y, Z and n have the abovementioned meaning

α) are reacted with chloromonothioformic esters or chlorodithioformic esters of the general formula (VI)

$$Cl-\underset{\underset{S}{\|}}{C}-M-R^2 \qquad (VI)$$

in which

M and $R^2$ have the abovementioned meaning, if appropriate in the presence of a diluent and if appropriate in the presence of an acid-binding agent, or β) are reacted with carbon disulphide and subsequently with alkyl halides of the general formula (VII)

$$R^2-Hal \qquad (VII)$$

in which $R^2$ has the abovementioned meaning and

Hal represents chlorine, bromine or iodine;

or (E) compounds of the formula (Id)

(Id)

[structure with Q, A, B—C—N, =O, R³—SO₂—O, X, Y, Z_n]

which

A, B, Q, X, Y, Z, $R^3$ and n have the abovementioned meaning are obtained when compounds of the formula (Ia)

(Ia)

[structure with Q, A, B—C—N, =O, HO, X, Y, Z_n]

in which

A, B, Q, X, Y, Z and n have the abovementioned meaning are reacted with sulphonyl chlorides of the general formula (VIII)

$$R^3-SO_2-Cl \qquad (VIII)$$

in which $R^3$ has the abovementioned meaning, if appropriate in the presence of a diluent and if appropriate in the presence of an acid-binding agent;

or (F) 3-aryl-pyrrolidine-2,4-diones of the formula (Ie)

(Ie)

[structure with Q, A, B—C—N, =O, R⁴/R⁵ P(=L)—O, X, Y, Z_n]

in which

A, B, Q, L, X, Y, Z, $R^4$, $R^5$ and n have the abovementioned meaning are obtained when 3-aryl-pyrrolidine-2,4-diones of the formula (Ia) or enols thereof (Ia)

[structure with Q, A, B—C—N, =O, HO, X, Y, Z_n]

in which

A, B, Q, X, Y, Z and n have the abovementioned meaning are reacted with phosphorus compounds of the general formula (IX)

(IX)

$$Hal-\underset{\underset{L}{\|}}{P}\diagdown{\overset{R^4}{R^5}}$$

in which

L, $R^4$ and $R^5$ have the abovementioned meaning and

Hal represents halogen, in particular chlorine and bromine;

or (G) compounds of the formula (If)

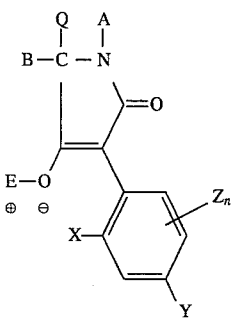

(If)

in which

A, B, Q, X, Y, z and n have the abovementioned meaning and

E represents a metal ion equivalent or an ammonium ion are obtained when compounds of the formula (Ia)

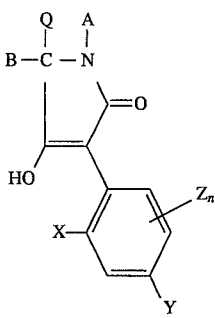

(Ia)

in which

A, B, Q, X, Y, Z and n have the abovementioned meaning are reacted with metal hydroxides or amines of the general formulae (X) and (XI)

$$Me_sOH_t \qquad (X)$$

(XI)

in which

Me represents mono- or divalent metal ions, s and t represent the number 1 and 2 and $R^5$, $R^6$ and $R^7$ independently of one another represent hydrogen and alkyl, if appropriate in the presence of a diluent.

Furthermore, it has been found that the new bicyclic 3-arylpyrrolidine-2,4-dione derivatives of the formula (I) are distinguished by outstanding insecticidal, acaricidal and hericidal activities.

The following applies to the general formulae of the present application:

A and Q together preferably represent an alkanediyl, alkenediyl, alkenedienyl or alkenetrienyl group having 3 to 6 carbon atoms, each of these groups being monosubstituted to trisubstituted by identical or different substituents, each of these groups being substituted by halogen, hydroxyl, mercapto, in each case optionally halogen-substituted alkyl having 1 to 10 carbon atoms, alkylcarbonyloxy having 1 to 8 carbon atoms, alkoxy having 1 to 6 carbon atoms, alkylthio having 1 to 6 carbon atoms, cycloalkyl having 3 to 7 carbon atoms or aryl having 6 to 10 carbon atoms and each of these groups additionally being interrupted, if appropriate, by one of the groups below:

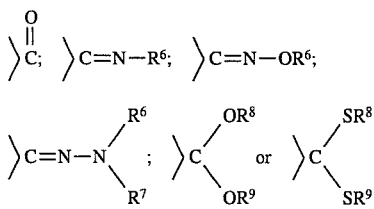

where $R^6$ and $R^7$ independently of one another represent hydrogen, optionally halogen-substituted $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl, or represent phenyl which is optionally substituted by halogen, $C_1$–$C_{20}$-halogenoalkyl, $C_1$–$C_{20}$-alkyl or $C_1$–$C_{20}$-alkoxy, or represent benzyl which is optionally substituted by halogen, $C_1$–$C_{20}$-alkyl, $C_1$–$C_{20}$-halogenoalkyl or $C_1$–$C_{20}$-alkoxy, or together represent a $C_2$–$C_6$-alkylene ring which is optionally interrupted by oxygen, $R^8$ and $R^9$ independently of one another represent hydrogen or alkyl having 1 to 6 carbon atoms, or $R^8$ and $R^9$ together represent an alkanediyl radical having 2 to 4 carbon atoms.

A and Q together particularly preferably represent an alkanediyl, alkenediyl or alkenedienyl group having 3 to 5 carbon atoms, each of these groups being monosubstituted to trisubstituted by identical or different substituents, each of these groups being substituted by fluorine, chlorine, bromine, hydroxyl, mercapto, in each case optionally halogen-substituted alkyl having 1 to 8 carbon atoms, alkylcarbonyloxy having 1 to 6 carbon atoms, alkoxy having 1 to 4 carbon atoms, alkylthio having 1 to 4 carbon atoms, cycloalkyl having 5 to 7 carbon atoms or phenyl, and each of these groups additionally being interrupted, if appropriate, by one of the groups below

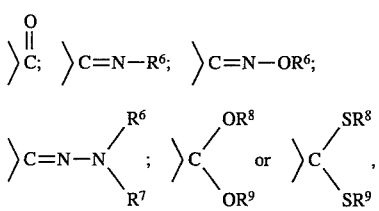

where $R^5$ and $R^7$ independently of one another represent hydrogen, optionally halogen-substituted $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, $R^8$ and $R^9$ independently of one another represent hydrogen or alkyl having 1 to 4 carbon atoms, or $R^8$ and $R^9$ together represent an alkanediyl radical having 2 or 3 carbon atoms.

A and Q together very particularly preferably represent an alkanediyl, alkenediyl or alkenedienyl group having 3 to 4 carbon atoms, each of these groups being monosubstituted to trisubstituted by identical or different substituents, each of these groups being substituted by fluorine, chlorine, bromine, hydroxyl, mercapto, in each case optionally fluorine-, chlorine- or bromine-substituted alkyl having 1 to 6 carbon atoms, alkylcarbonyloxy having 1 to 4 carbon atoms, alkoxy having 1 to 2 carbon atoms, alkylthio having 1 or 2 carbon atoms or cycloalkyl having 5 or 6 carbon atoms, and each of these groups additionally being interrupted, if appropriate, by one of the groups below

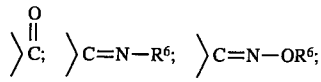

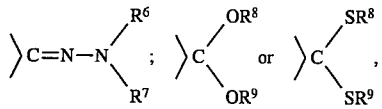

where

R$^6$ and R$^7$ independently of one another represents optionally fluorine-, chlorine- or bromine-substituted C$_1$–C$_{10}$-alkyl, C$_1$–C$_{10}$-alkoxy or C$_1$–C$_{10}$-alkoxy(C$_1$–C$_{10}$)-alkyl, or represents phenyl which is optionally substituted by fluorine, chlorine, bromine, C$_1$–C$_{20}$-halogenoalkyl, C$_1$–C$_{20}$-alkyl or C$_1$–C$_4$-alkoxy, or represents benzyl which is optionally substituted by fluorine, chlorine, bromine, C$_1$–C$_4$-alkyl, C$_1$–C$_4$-halogenoalkyl or C$_1$–C$_4$-alkoxy, R$^8$ and R$^9$ independently of one another represent hydrogen or alkyl having 1 to 4 carbon atoms, or R$^8$ and R$^9$ together represent an alkanediyl radical having 2 or 3 carbon atoms.

B preferably represents hydrogen or alkyl having 1 to 6 carbon atoms.

B particularly preferably represents hydrogen or alkyl having 1 to 4 carbon atoms.

B very particularly preferably represents hydrogen, methyl or ethyl.

X preferably represents C$_1$–C$_6$-alkyl, halogen or C$_1$–C$_6$-alkoxy.

X particularly preferably represents C$_1$–C$_4$-alkyl, halogen or C$_1$–C$_4$-alkoxy.

X very particularly preferably represents methyl, ethyl, propyl, 2-propyl, fluorine, chlorine, bromine, methoxy or ethoxy.

Y preferably represents hydrogen, C$_1$–C$_6$-alkyl, halogen, C$_1$–C$_6$-alkoxy or C$_1$–C$_3$-halogenoalkyl.

Y particularly preferably represents hydrogen, C$_1$–C$_4$-alkyl, halogen, C$_1$–C$_4$-alkoxy or C$_1$–C$_2$-halogenoalkyl.

Y very particularly preferably represents hydrogen, methyl, ethyl, propyl, i-propyl, butyl, i-butyl, tert.-butyl, fluorine, chlorine, bromine, methoxy, ethoxy or trifluoromethyl.

Z preferably represents C$_1$–C$_6$-alkyl, halogen or C$_1$–C$_6$-alkoxy.

Z particularly preferably represents C$_1$–C$_4$-alkyl, halogen or C$_1$–C$_4$-alkoxy.

Z very particularly preferably represents methyl, ethyl, propyl, i-propyl, butyl, i-butyl, tert.-butyl, fluorine, chlorine, bromine, methoxy or ethoxy.

G preferably represents hydrogen (a) or the groups $-CO-R^1$, (b)

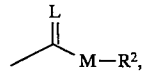

$-SO_2-R^3$, (d)

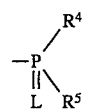

or

E (f)

in which

E represents a metal ion equivalent or an ammonium ion,

L and M represents oxygen and/or sulphur,

R$^1$ represents optionally halogen-substituted C$_1$–C$_{20}$-alkyl, C$_2$–C$_{20}$-alkenyl, C$_1$–C$_8$-alkoxy-C$_2$–C$_8$-alkyl, C$_1$–C$_8$-alkylthio-C$_2$–C$_8$-alkyl, C$_1$–C$_8$-polyalkoxy-C$_2$–C$_8$-alkyl or cycloalkyl which have 3 to 8 ring atoms and which can be interrupted by oxygen and/or sulphur atoms, or represents phenyl which is optionally substituted by halogen, nitro, C$_1$–C$_6$-alkyl, C$_1$–C$_6$-alkoxy, C$_1$–C$_6$-halogenoalkyl or C$_1$–C$_6$-halogenoalkoxy-, or represents phenyl-C$_1$–C$_6$-alkyl which is optionally substituted by halogen, C$_1$–C$_6$-alkyl, C$_1$–C$_6$-alkoxy, C$_1$–C$_6$-halogenoalkyl or C$_1$–C$_6$-halogenoalkoxy, or represents hetaryl which is optionally substituted by halogen and/or C$_1$–C$_6$-alkyl, or represents phenoxy-C$_1$–C$_6$-alkyl which is optionally substituted by halogen and C$_1$–C$_6$-alkyl-, or represents hetaryloxy-C$_1$–C$_6$-alkyl which is optionally substituted by halogen, amino and C$_1$–C$_6$-alkyl-, R$^2$ represents optionally halogen-substituted C$_1$–C$_{20}$-alkyl, C$_2$–C$_{20}$-alkenyl, C$_1$–C$_8$-alkoxy-C$_2$–C$_8$-alkyl or C$_1$–C$_8$-polyalkoxy-C$_2$–C$_8$-alkyl, or represents phenyl or benzyl which are optionally substituted by halogen, nitro, C$_1$–C$_6$-alkyl, C$_1$C$_6$-alkoxy or C$_1$–C$_6$-halogenoalkyl-, R$^3$, R$^4$ and R$^5$ independently of one another represent optionally halogen-substituted C$_1$–C$_8$-alkyl, C$_1$–C$_8$-alkoxy, C$_1$–C$_8$-alkylamino, di-(C$_1$–C$_8$)-alkylamino, C$_1$–C$_8$-alkylthio, C$_2$–C$_5$-alkenylthio, C$_2$–C$_5$-alkinylthio or C$_3$–C$_7$-cycloalkylthio, or represent phenyl, phenoxy or phenylthio which are optionally substituted by halogen, nitro, cyano, C$_1$–C$_4$-alkoxy, C$_1$–C$_4$-halogenoalkoxy, C$_1$–C$_4$-alkylthio, C$_1$–C$_4$-halogenoalkylthio, C$_1$–C$_4$-alkyl or C$_1$–C$_4$-halogenoalkyl, G particularly preferably represents hydrogen (a) or the groups $-CO-R^1$, (b)

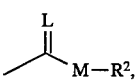

$-SO_2-R^3$, (d)

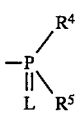

or

E (f)

in which

E represents a metal ion equivalent or an ammonium ion,

L and M in each case represents oxygen and/or sulphur, $R^1$ represents optionally halogen-substituted $C_1$–$C_{16}$-alkyl, $C_2$–$C_{16}$-alkenyl, $C_1$–$C_6$-alkoxy-$C_2$–$C_6$-alkyl, $C_1$–$C_{16}$-alkylthio-$C_2$–$C_6$-alkyl, $C_1$–$C_6$-polyalkoxy-$C_2$–$C_6$-alkyl or cycloalkyl which have 3 to 7 ring atoms and which can be interrupted by 1–2 oxygen and/or sulphur atoms, or represents phenyl which is optionally substituted by halogen-, nitro-, $C_1$–$C_4$-alkyl-, $C_1$–$C_4$-alkoxy-, $C_1$–$C_3$-halogenoalkyl- or $C_1$–$C_3$-halogenoalkoxy-, or represents phenyl-$C_1$–$C_4$-alkyl which is optionally substituted by halogen-, $C_1$–$C_4$-alkyl-, $C_1$–$C_4$-alkoxy-, $C_1$–$C_3$-halogenoalkyl- or $C_1$–$C_3$-halogenoalkoxy-, or represents hetaryl which is optionally substituted by halogen- and/or $C_1$–$C_6$-alkyl-, or represents phenoxy-$C_1$–$C_5$-alkyl which is optionally substituted by halogen- and $C_1$–$C_4$-alkyl-, or represents hetaryloxy-$C_1$–$C_5$-alkyl which is optionally substituted by halogen, amino and $C_1$–$C_4$-alkyl-, $R^2$ represents optionally halogen-substituted $C_1$–$C_{16}$-alkyl, $C_2$–$C_{16}$-alkenyl, $C_1$–$C_{16}$-alkoxy-$C_2$–$C_6$-alkyl or $C_1$–$C_6$-polyalkoxy-$C_2$–$C_6$-alkyl, or represents phenyl or benzyl which are optionally substituted by halogen-, nitro-, $C_1$–$C_4$-alkyl-, $C_1$–$C_3$-alkoxy- or $C_1$–$C_3$-halogenoalkyl-, $R^3$, $R^4$ and $R^5$ independently of one another represent optionally halogen-substituted $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio, $C_2$–$C_4$-alkinylthio or $C_3$–$C_6$-cycloalkylthio, or represent phenyl, phenoxy or phenylthio which are optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

G very particularly preferably represents hydrogen (a) or the groups $-CO-R^1$, (b)

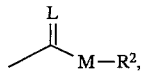 (c)

$-SO_2-R^3$, (d)

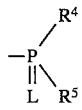 (e)

or

E (f)

in which

E represents a metal ion equivalent or an ammonium ion,

L and M represent oxygen and/or sulphur, $R^1$ represents optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl, $C_1$–$C_4$-alkylthio-$C_2$–$C_6$-alkyl, $C_1$–$C_4$-polyalkoxy-$C_2$–$C_4$-alkyl or cycloalkyl which has 3 to 6 ring atoms and which can be interrupted by 1 to 2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy or nitro-, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy-, or represents pyridyl, pyrimidyl, thiazolyl and pyrazolyl which are optionally substituted by fluorine, chlorine, bromine, methyl or ethyl-, or represents phenoxy-$C_1$–$C_4$-alkyl which is optionally substituted by fluorine, chlorine, methyl or ethyl-, or represents pyridyloxy-$C_1$–$C_4$-alkyl, pyrimidyloxy-$C_1$–$C_4$-alkyl and thiazolyloxy-$C_1$–$C_4$-alkyl which are optionally substituted by fluorine, chlorine, amino, methyl- or ethyl, $R^2$ represents $C_1$–$C_{14}$-alkyl, $C_2$–$C_{14}$-alkenyl, $C_1$–$C_4$-alkoxy-$C_2$–$C_6$-alkyl or $C_1$–$C_4$-polyaloxy-$C_2$–$C_6$-alkyl which are optionally substituted by fluorine or chlorine, or represents phenyl or benzyl which are optionally substituted by fluorine, chlorine, nitro, methyl, ethyl, propyl, i-propyl, methoxy, ethoxy, trifluoromethyl, $R^3$, $R^4$ and $R^5$ independently of one another represent $C_1$–$C_4$-alkyl, $C_1$–$C_4$-alkoxy, $C_1$–$C_4$-alkyl-amino, di-($C_1$–$C_4$)-alkylamino or $C_1$–$C_4$-alkylthio which are optionally substituted by fluorine or chlorine, or represent phenyl, phenoxy or phenylthio which are optionally substituted by fluorine, chlorine, bromine, nitro, cyano, $C_1$–$C_2$-alkoxy, $C_1$–$C_4$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl.

Preferred bicyclic 3-aryl-pyrrolidine-2,4-diones of the formula (I) are those in which n represents a number 0, 1, 2 or 3 and the radicals A, Q, B, G, X, Y and Z in each case have the meanings given above as being preferred.

Particularly preferred bicyclic 3-aryl-pyrrolidine-2,4-diones of the formula (I) are those in which n represents a number 0, 1, 2 or 3 and the radicals A, Q, B, G, X, Y and Z in each case have the meanings given above as being particularly preferred.

Very particularly preferred bicyclic 3-aryl-pyrrolidine-2,4-diones of the formula (I) are those in which n represents a number 0, 1, 2 or 3 and the radicals A, Q, B, G, X, Y and Z in each case have the meanings given above as being very particularly preferred.

In addition to the compounds mentioned in the Preparation Examples, the following substituted bicyclic 3-aryl-pyrrolidine-2,4-dione derivatives of the general formula (I) may be mentioned individually:

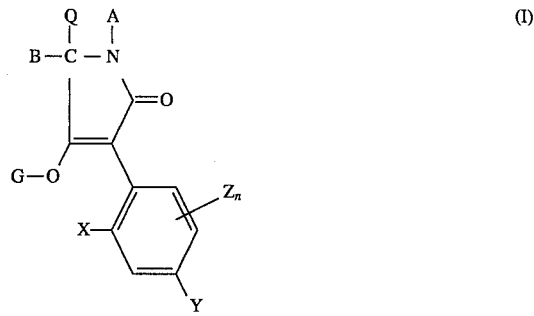

TABLE 1

| A Q | B | X | Y | $Z_n$ | G |
|---|---|---|---|---|---|
| $-CH(CH_3)-CH(CH_3)-CH_2-$ | H | Cl | Cl | H | H |
| $-CH(CH_3)-CH(CH_3)-CH_2-$ | H | Cl | H | 6-Cl | H |
| $-CH(CH_3)-CH(CH_3)-CH_2-$ | H | $CH_3$ | $CH_3$ | H | H |
| $-CH(CH_3)-CH(CH_3)-CH_2-$ | H | $CH_3$ | H | 6-$CH_3$ | H |
| $-CH(CH_3)-CH(CH_3)-(CH_2)_2-$ | H | Cl | Cl | H | H |
| $-CH(CH_3)-CH(CH_3)-(CH_2)_2-$ | H | Cl | H | 6-Cl | H |
| $-CH(CH_3)-CH(CH_3)-(CH_2)_2-$ | H | $CH_3$ | $CH_3$ | H | H |
| $-CH(CH_3)-CH(CH_3)-(CH_2)_2-$ | H | $CH_3$ | H | 6-$CH_3$ | H |
| $-CH(CH_3)-CH(CH_3)-(CH_2)_2-$ | H | $CH_3$ | $CH_3$ | 6-$CH_3$ | H |
| $-CH(CH_3)-CH(CH_3)-CH_2-$ | H | Cl | Cl | H | $CH_3-\overset{\overset{O}{\|}}{C}-$ |
| $-CH(CH_3)-CH(CH_3)-CH_2-$ | H | Cl | Cl | H | $(CH_3)_3C-\overset{\overset{O}{\|}}{C}-$ |
| $-CH(CH_3)-CH(CH_3)-CH_2-$ | H | Cl | H | 6-Cl | $CH_3-\overset{\overset{O}{\|}}{C}-$ |
| $-CH(CH_3)-CH(CH_3)-CH_2-$ | H | Cl | H | 6-Cl | $(CH_3)_3C-\overset{\overset{O}{\|}}{C}-$ |
| $-CH(CH_3)-CH(CH_3)-CH_2-$ | H | $CH_3$ | $CH_3$ | H | $CH_3-\overset{\overset{O}{\|}}{C}-$ |
| $-CH(CH_3)-CH(CH_3)-CH_2-$ | H | $CH_3$ | $CH_3$ | H | $(CH_3)_3C-\overset{\overset{O}{\|}}{C}-$ |
| $-CH(CH_3)-CH(CH_3)-CH_2-$ | H | $CH_3$ | H | 6-$CH_3$ | $CH_3-\overset{\overset{O}{\|}}{C}-$ |
| $-CH(CH_3)-CH(CH_3)-(CH_2)_2-$ | H | Cl | Cl | H | $CH_3-\overset{\overset{O}{\|}}{C}-$ |
| $-CH(CH_3)-CH(CH_3)-(CH_2)_2-$ | H | Cl | Cl | H | $(CH_3)_3C-\overset{\overset{O}{\|}}{C}-$ |
| $-CH(CH_3)-CH(CH_3)-(CH_2)_2-$ | H | Cl | H | 6-Cl | $CH_3-\overset{\overset{O}{\|}}{C}-$ |
| $-CH(CH_3)-CH(CH_3)-(CH_2)_2-$ | H | Cl | H | 6-Cl | $(CH_3)_3C-\overset{\overset{O}{\|}}{C}-$ |
| $-CH(CH_3)-CH(CH_3)-(CH_2)_2-$ | H | $CH_3$ | $CH_3$ | H | $CH_3-\overset{\overset{O}{\|}}{C}-$ |
| $-CH(CH_3)-CH(CH_3)-(CH_2)_2-$ | H | $CH_3$ | $CH_3$ | H | $(CH_3)_3C-\overset{\overset{O}{\|}}{C}-$ |
| $-CH(CH_3)-CH(CH_3)-(CH_2)_2-$ | H | $CH_3$ | H | 6-$CH_3$ | $CH_3-\overset{\overset{O}{\|}}{C}-$ |
| $-CH(CH_3)-CH(CH_3)-CH_2-$ | H | $CH_3$ | H | 6-$CH_3$ | $(CH_3)_3C-\overset{\overset{O}{\|}}{C}-$ |
| $-CH(CH_3)-CH(CH_3)-CH_2-$ | H | $CH_3$ | $CH_3$ | 6-$CH_3$ | $(CH_3)_2CH-\overset{\overset{O}{\|}}{C}-$ |
| $-CH(CH_3)-CH(CH_3)-CH_2-$ | H | $CH_3$ | $CH_3$ | 6-$CH_3$ | $CH_3-(CH_2)_3-\overset{\overset{O}{\|}}{C}-$ |
| $-CH(CH_3)-CH(CH_3)-CH_2-$ | H | $CH_3$ | $CH_3$ | 6-$CH_3$ | $\underset{C_2H_5-C(CH_3)_2}{-\overset{\|}{C}=O}$ |

TABLE 1-continued

| A Q | B | X | Y | $Z_n$ | G |
|---|---|---|---|---|---|
| —CH(CH$_3$)—CH(CH$_3$)—CH$_2$— | H | CH$_3$ | CH$_3$ | 6-CH$_3$ | (CH$_3$)$_3$C—CH$_2$—C(=O)— |
| —CH(CH$_3$)—CH(CH$_3$)—CH$_2$— | H | CH$_3$ | CH$_3$ | 6-CH$_3$ | (CH$_3$)$_2$CH—C(CH$_3$)$_2$—C(=O)— |
| —CH(CH$_3$)—CH(CH$_3$)—CH$_2$— | H | CH$_3$ | CH$_3$ | 6-CH$_3$ | CH$_2$=CH—(CH$_2$)$_8$—C(=O)— |
| —CH(CH$_3$)—CH(CH$_3$)—CH$_2$— | H | CH$_3$ | CH$_3$ | 6-CH$_3$ | (Cl—CH$_2$)(H$_3$C—CH$_2$)(CH$_3$)C—C(=O)— |
| —CH(CH$_3$)—CH(CH$_3$)—(CH$_2$)$_2$— | H | CH$_3$ | H | 6-CH$_3$ | (CH$_3$)$_3$C—C(=O)— |
| —CH(CH$_3$)—CH(CH$_3$)—(CH$_2$)$_2$— | H | CH$_3$ | CH$_3$ | 6-CH$_3$ | (CH$_3$)$_2$CH—C(=O)— |
| —CH(CH$_3$)—CH(CH$_3$)—(CH$_2$)$_2$— | H | CH$_3$ | CH$_3$ | 6-CH$_3$ | CH$_3$—(CH$_2$)$_3$—C(=O)— |
| —CH(CH$_3$)—CH(CH$_3$)—(CH$_2$)$_2$— | H | CH$_3$ | CH$_3$ | 6-CH$_3$ | C$_2$H$_5$—C(CH$_3$)$_2$—C(=O)— |
| —CH(CH$_3$)—CH(CH$_3$)—(CH$_2$)$_2$— | H | CH$_3$ | CH$_3$ | 6-CH$_3$ | (CH$_3$)$_3$C—CH$_2$—C(=O)— |
| —CH(CH$_3$)—CH(CH$_3$)—(CH$_2$)$_2$— | H | CH$_3$ | CH$_3$ | 6-CH$_3$ | (CH$_3$)$_2$CH—C(CH$_3$)$_2$—C(=O)— |
| —CH(CH$_3$)—CH(CH$_3$)—(CH$_2$)$_2$— | H | CH$_3$ | CH$_3$ | 6-CH$_3$ | CH$_2$=CH—(CH$_2$)$_8$—C(=O)— |
| —CH(CH$_3$)—CH(CH$_3$)—(CH$_2$)$_2$— | H | CH$_3$ | CH$_3$ | 6-CH$_3$ | (Cl—CH$_2$)(H$_3$C—CH$_2$)(CH$_3$)C—C(=O)— |
| —CH(CH$_3$)—CH(CH$_3$)—CH$_2$— | H | CH$_3$ | CH$_3$ | 6-CH$_3$ | (Cl—CH$_2$)$_2$(CH$_3$)C—C(=O)— |
| —CH(CH$_3$)—CH(CH$_3$)—CH$_2$— | H | CH$_3$ | CH$_3$ | 6-CH$_3$ | (H$_3$C—O—CH$_2$)(H$_3$C)(CH$_3$)C—C(=O)— |
| —CH(CH$_3$)—CH(CH$_3$)—CH$_2$— | H | CH$_3$ | CH$_3$ | 6-CH$_3$ | (H$_3$C—O—CH$_2$)$_2$(CH$_3$)C—C(=O)— |

TABLE 1-continued

| A Q | B | X | Y | $Z_n$ | G |
|---|---|---|---|---|---|
| —CH(CH$_3$)—CH(CH$_3$)—CH$_2$— | H | CH$_3$ | CH$_3$ | 6-CH$_3$ | (CH$_3$)$_2$C=CH—C(=O)— |
| —CH(CH$_3$)—CH(CH$_3$)—CH$_2$— | H | CH$_3$ | CH$_3$ | 6-CH$_3$ | H$_3$C—S—CH$_2$—C(=O)— |
| —CH(CH$_3$)—CH(CH$_3$)—CH$_2$— | H | CH$_3$ | CH$_3$ | 6-CH$_3$ | 5-methyl-1,3-dioxan-5-yl-C(=O)— (H$_3$C substituent) |
| —CH(CH$_3$)—CH(CH$_3$)—(CH$_2$)$_2$— | H | CH$_3$ | CH$_3$ | 6-CH$_3$ | (ClCH$_2$)$_2$C(CH$_3$)—C(=O)— |
| —CH(CH$_3$)—CH(CH$_3$)—(CH$_2$)$_2$— | H | CH$_3$ | CH$_3$ | 6-CH$_3$ | (H$_3$COCH$_2$)(CH$_3$)$_2$C—C(=O)— |
| —CH(CH$_3$)—CH(CH$_3$)—(CH$_2$)$_2$— | H | CH$_3$ | CH$_3$ | 6-CH$_3$ | (H$_3$COCH$_2$)$_2$C(CH$_3$)—C(=O)— |
| —CH(CH$_3$)—CH(CH$_3$)—(CH$_2$)$_2$— | H | CH$_3$ | CH$_3$ | 6-CH$_3$ | (CH$_3$)$_2$C=CH—C(=O)— |
| —CH(CH$_3$)—CH(CH$_3$)—(CH$_2$)$_2$— | H | CH$_3$ | CH$_3$ | 6-CH$_3$ | H$_3$C—S—CH$_2$—C(=O)— |
| —CH(CH$_3$)—CH(CH$_3$)—(CH$_2$)$_2$— | H | CH$_3$ | CH$_3$ | 6-CH$_3$ | 5-methyl-1,3-dioxan-5-yl-C(=O)— (H$_3$C substituent) |
| —CH(CH$_3$)—CH(CH$_3$)—CH$_2$— | H | CH$_3$ | CH$_3$ | 6-CH$_3$ | 5-ethyl-1,3-dioxan-5-yl-C(=O)— (C$_2$H$_5$ substituent) |
| —CH(CH$_3$)—CH(CH$_3$)—CH$_2$— | H | CH$_3$ | CH$_3$ | 6-CH$_3$ | 2-(H$_3$CO)C$_6$H$_4$—C(=O)— |

TABLE 1-continued

| A Q | B | X | Y | $Z_n$ | G |
|---|---|---|---|---|---|
| —CH(CH₃)—CH(CH₃)—CH₂— | H | CH₃ | CH₃ | 6-CH₃ | 3-methoxybenzoyl (O=C— attached to phenyl with H₃CO at meta) |
| —CH(CH₃)—CH(CH₃)—CH₂— | H | CH₃ | CH₃ | 6-CH₃ | 4-methoxybenzoyl (O=C— attached to phenyl with OCH₃ at para) |
| —CH(CH₃)—CH(CH₃)—(CH₂)₂— | H | CH₃ | CH₃ | 6-CH₃ | 5-ethyl-1,3-dioxan-5-yl carbonyl (C₂H₅ and C=O on ring carbon with two O—CH₂) |
| —CH(CH₃)—CH(CH₃)—(CH₂)₂— | H | CH₃ | CH₃ | 6-CH₃ | 2-methoxybenzoyl (O=C— attached to phenyl with H₃CO at ortho) |
| —CH(CH₃)—CH(CH₃)—(CH₂)₂— | H | CH₃ | CH₃ | 6-CH₃ | 3-methoxybenzoyl (O=C— attached to phenyl with H₃CO at meta) |
| —CH(CH₃)—CH(CH₃)—(CH₂)₂— | H | CH₃ | CH₃ | 6-CH₃ | 4-methoxybenzoyl (O=C— attached to phenyl with OCH₃ at para) |
| —CH(CH₃)—CH(CH₃)—CH₂— | H | Cl | Cl | H | $$\mathrm{C_2H_5-O-\overset{\overset{O}{\|}}{C}-}$$ |
| —CH(CH₃)—CH(CH₃)—CH₂— | H | Cl | H | 6-Cl | $$\mathrm{C_2H_5-O-\overset{\overset{O}{\|}}{C}-}$$ |
| —CH(CH₃)—CH(CH₃)—CH₂— | H | CH₃ | CH₃ | H | $$\mathrm{C_2H_5-O-\overset{\overset{O}{\|}}{C}-}$$ |
| —CH(CH₃)—CH(CH₃)—CH₂— | H | CH₃ | H | 6-CH₃ | $$\mathrm{C_2H_5-O-\overset{\overset{O}{\|}}{C}-}$$ |
| —CH(CH₃)—CH(CH₃)—CH₂— | H | CH₃ | CH₃ | 6-CH₃ | $$\mathrm{CH_3-O-\overset{\overset{O}{\|}}{C}-}$$ |
| —CH(CH₃)—CH(CH₃)—CH₂— | H | CH₃ | CH₃ | 6-CH₃ | $$\mathrm{C_2H_5-O-\overset{\overset{O}{\|}}{C}-}$$ |
| —CH(CH₃)—CH(CH₃)—CH₂— | H | CH₃ | CH₃ | 6-CH₃ | $$\mathrm{(CH_3)_2CH-O-\overset{\overset{O}{\|}}{C}-}$$ |
| —CH(CH₃)—CH(CH₃)—(CH₂)₂— | H | Cl | Cl | H | $$\mathrm{C_2H_5-O-\overset{\overset{O}{\|}}{C}-}$$ |

TABLE 1-continued

| A Q | B | X | Y | $Z_n$ | G |
|---|---|---|---|---|---|
| —CH(CH$_3$)—CH(CH$_3$)—(CH$_2$)$_2$— | H | Cl | H | 6-Cl | $C_2H_5-O-\overset{\overset{O}{\|\|}}{C}-$ |
| —CH(CH$_3$)—CH(CH$_3$)—(CH$_2$)$_2$— | H | CH$_3$ | CH$_3$ | H | $C_2H_5-O-\overset{\overset{O}{\|\|}}{C}-$ |
| —CH(CH$_3$)—CH(CH$_3$)—(CH$_2$)$_2$— | H | CH$_3$ | H | 6-CH$_3$ | $C_2H_5-O-\overset{\overset{O}{\|\|}}{C}-$ |
| —CH(CH$_3$)—CH(CH$_3$)—(CH$_2$)$_2$— | H | CH$_3$ | CH$_3$ | 6-CH$_3$ | $CH_3-O-\overset{\overset{O}{\|\|}}{C}-$ |
| —CH(CH$_3$)—CH(CH$_3$)—(CH$_2$)$_2$— | H | CH$_3$ | CH$_3$ | 6-CH$_3$ | $C_2H_5-O-\overset{\overset{O}{\|\|}}{C}-$ |
| —CH(CH$_3$)—CH(CH$_3$)—(CH$_2$)$_2$— | H | CH$_3$ | CH$_3$ | 6-CH$_3$ | $(CH_3)_2CH-O-\overset{\overset{O}{\|\|}}{C}-$ |
| —CH(CH$_3$)—CH(CH$_3$)—CH$_2$— | H | CH$_3$ | CH$_3$ | 6-CH$_3$ | $(CH_3)_2CH-CH_2-O-\overset{\overset{O}{\|\|}}{C}-$ |
| —CH(CH$_3$)—CH(CH$_3$)—CH$_2$— | H | CH$_3$ | CH$_3$ | 6-CH$_3$ | $C_2H_5-\overset{\overset{CH_3}{\|}}{CH}-O-\overset{\overset{O}{\|\|}}{C}-$ |
| —CH(CH$_3$)—CH(CH$_3$)—CH$_2$— | H | CH$_3$ | CH$_3$ | 6-CH$_3$ | $(CH_3)_3C-O-\overset{\overset{O}{\|\|}}{C}-$ |
| —CH(CH$_3$)—CH(CH$_3$)—CH$_2$— | H | CH$_3$ | CH$_3$ | 6-CH$_3$ | $(CH_3)_3C-CH_2-O-\overset{\overset{O}{\|\|}}{C}-$ |
| —CH(CH$_3$)—CH(CH$_3$)—CH$_2$— | H | CH$_3$ | CH$_3$ | 6-CH$_3$ | 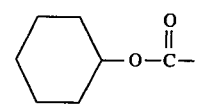 |
| —CH(CH$_3$)—CH(CH$_3$)—CH$_2$— | H | CH$_3$ | CH$_3$ | 6-CH$_3$ | $C_2H_5O-(CH_2)_2-O-\overset{\overset{O}{\|\|}}{C}-$ |
| —CH(CH$_3$)—CH(CH$_3$)—CH$_2$— | H | CH$_3$ | CH$_3$ | 6-CH$_3$ | $C_2H_5O-(CH_2)_2-O-CH_2-O-\overset{\overset{O}{\|\|}}{C}-$ |
| —CH(CH$_3$)—CH(CH$_3$)—CH$_2$— | H | CH$_3$ | CH$_3$ | 6-CH$_3$ | 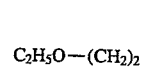 |
| —CH(CH$_3$)—CH(CH$_3$)—(CH$_2$)$_2$— | H | CH$_3$ | CH$_3$ | 6-CH$_3$ | $(CH_3)_2CH-CH_2-O-\overset{\overset{O}{\|\|}}{C}-$ |
| —CH(CH$_3$)—CH(CH$_3$)—(CH$_2$)$_2$— | H | CH$_3$ | CH$_3$ | 6-CH$_3$ | $C_2H_5-\overset{\overset{CH_3}{\|}}{CH}-O-\overset{\overset{O}{\|\|}}{C}-$ |
| —CH(CH$_3$)—CH(CH$_3$)—(CH$_2$)$_2$— | H | CH$_3$ | CH$_3$ | 6-CH$_3$ | $(CH_3)_3C-O-\overset{\overset{O}{\|\|}}{C}-$ |
| —CH(CH$_3$)—CH(CH$_3$)—(CH$_2$)$_2$— | H | CH$_3$ | CH$_3$ | 6-CH$_3$ | $(CH_3)_3C-CH_2-O-\overset{\overset{O}{\|\|}}{C}-$ |
| —CH(CH$_3$)—CH(CH$_3$)—(CH$_2$)$_2$— | H | CH$_3$ | CH$_3$ | 6-CH$_3$ | 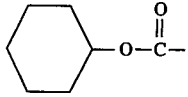 |

TABLE 1-continued

| A | Q | B | X | Y | $Z_n$ | G |
|---|---|---|---|---|---|---|
| | $-CH(CH_3)-CH(CH_3)-(CH_2)_2-$ | H | $CH_3$ | $CH_3$ | 6-$CH_3$ | $C_2H_5O-(CH_2)_2-O-\overset{O}{\underset{\parallel}{C}}-$ |
| | $-CH(CH_3)-CH(CH_3)-CH_2-$ | H | $CH_3$ | $CH_3$ | 6-$CH_3$ | $C_6H_5-O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | $(CH_3)_2CH-CH_2-O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | $C_2H_5-\overset{CH_3}{\underset{\vert}{CH}}-O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | $(CH_3)_3C-O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | $(CH_3)_3C-CH_2-O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | cyclohexyl-$O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | $C_2H_5O-(CH_2)_2-O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | $C_2H_5O-(CH_2)_2-O-CH_2-O-\overset{O}{\underset{\parallel}{C}}-$ |
| | $-CH(CH_3)-CH(CH_3)-(CH_2)_2-$ | H | $CH_3$ | $CH_3$ | 6-$CH_3$ | $C_6H_5-O-\overset{O}{\underset{\parallel}{C}}-$ |
| | $-CH_2-\underset{S\diagdown\;\;\diagup S}{C}-CH_2-$ | H | $CH_3$ | $CH_3$ | 6-$CH_3$ | H |
| | $-CH_2-\underset{S\diagdown\;\;\diagup S}{C}-CH_2-$ | H | $CH_3$ | $CH_3$ | 6-$CH_3$ | $-COCH_3$ |
| | $-CH_2-\underset{S\diagdown\;\;\diagup S}{C}-CH_2-$ | H | $CH_3$ | $CH_3$ | 6-$CH_3$ | $-CO-CH(CH_3)_2$ |
| | $-CH_2-\underset{S\diagdown\;\;\diagup S}{C}-CH_2-$ | H | $CH_3$ | $CH_3$ | 6-$CH_3$ | $-CO-C(CH_3)_3$ |
| | $-CH_2-\underset{S\diagdown\;\;\diagup S}{C}-CH_2-$ | H | $CH_3$ | $CH_3$ | 6-$CH_3$ | $-\underset{\underset{O}{\parallel}}{C}-OCH_3$ |
| | $-CH_2-\underset{S\diagdown\;\;\diagup S}{C}-CH_2-$ | H | $CH_3$ | $CH_3$ | 6-$CH_3$ | $-\underset{\underset{O}{\parallel}}{C}-O-CH(CH_3)_2$ |
| | $-CH_2-\underset{S\diagdown\;\;\diagup S}{C}-CH_2-$ | H | $CH_3$ | $CH_3$ | 6-$CH_3$ | $-\underset{\underset{O}{\parallel}}{C}-O-CH_2-CH(CH_3)_2$ |

TABLE 1-continued

| A Q | B | X | Y | $Z_n$ | G |
|---|---|---|---|---|---|
| −CH₂−C−CH₂− with S−S bridge (5-membered dithiolane) | H | CH₃ | CH₃ | 6-CH₃ | −C(=O)−O−CH(C₂H₅)(CH₃) |
| −CH₂−C−CH₂− with S−S bridge (5-membered dithiolane) | H | CH₃ | CH₃ | 6-CH₃ | −C(=O)−O−C(CH₃)₃ |
| −CH₂−C−CH₂− with S−S bridge (5-membered dithiolane) | H | CH₃ | CH₃ | 6-CH₃ | −C(=O)−C₆H₅ |
| −CH₂−C−CH₂− with S−CH₂−CH₂−S bridge (6-membered dithiane) | H | CH₃ | CH₃ | 6-CH₃ | H |
| −CH₂−C−CH₂− with S−CH₂−CH₂−S bridge | H | CH₃ | CH₃ | 6-CH₃ | −COCH₃ |
| −CH₂−C−CH₂− with S−CH₂−CH₂−S bridge | H | CH₃ | CH₃ | 6-CH₃ | −CO−CH(CH₃)₂ |
| −CH₂−C−CH₂− with S−CH₂−CH₂−S bridge | H | CH₃ | CH₃ | 6-CH₃ | −CO−C(CH₃)₃ |
| −CH₂−C−CH₂− with S−CH₂−CH₂−S bridge | H | CH₃ | CH₃ | 6-CH₃ | −C(=O)−O−OCH₃ |
| −CH₂−C−CH₂− with S−CH₂−CH₂−S bridge | H | CH₃ | CH₃ | 6-CH₃ | −C(=O)−O−CH(CH₃)₂ |
| −CH₂−C−CH₂− with S−CH₂−CH₂−S bridge | H | CH₃ | CH₃ | 6-CH₃ | −C(=O)−O−CH₂−CH(CH₃)₂ |
| −CH₂−C−CH₂− with S−CH₂−CH₂−S bridge | H | CH₃ | CH₃ | 6-CH₃ | −C(=O)−O−CH(C₂H₅)(CH₃) |
| −CH₂−C−CH₂− with S−CH₂−CH₂−S bridge | H | CH₃ | CH₃ | 6-CH₃ | −C(=O)−O−C(CH₃)₃ |
| −CH₂−C−CH₂− with S−CH₂−CH₂−S bridge | H | CH₃ | CH₃ | 6-CH₃ | −C(=O)−C₆H₅ |
| −CH₂−C(=N−NH₂)−CH₂− | H | CH₃ | CH₃ | 6-CH₃ | H |

TABLE 1-continued

| A Q | B | X | Y | $Z_n$ | G |
|---|---|---|---|---|---|
| —CH$_2$—C(=N—NH$_2$)—CH$_2$— | H | CH$_3$ | CH$_3$ | 6-CH$_3$ | —COCH$_3$ |
| —CH$_2$—C(=N—NH$_2$)—CH$_2$— | H | CH$_3$ | CH$_3$ | 6-CH$_3$ | —CO—C(CH$_3$)$_3$ |
| —CH$_2$—C(=N—NH$_2$)—CH$_2$— | H | CH$_3$ | CH$_3$ | 6-CH$_3$ | —C(=O)—OCH$_3$ |
| —CH$_2$—C(=N—NH$_2$)—CH$_2$— | H | CH$_3$ | CH$_3$ | 6-CH$_3$ | —C(=O)—OCH(CH$_3$)$_2$ |
| —CH$_2$—C(=N—NHCH$_3$)—CH$_2$— | H | CH$_3$ | CH$_3$ | 6-CH$_3$ | H |
| —CH$_2$—C(=N—NHCH$_3$)—CH$_2$— | H | CH$_3$ | CH$_3$ | 6-CH$_3$ | —COCH$_3$ |
| —CH$_2$—C(=N—NHCH$_3$)—CH$_2$— | H | CH$_3$ | CH$_3$ | 6-CH$_3$ | —COC(CH$_3$)$_3$ |
| —CH$_2$—C(=N—NHCH$_3$)—CH$_2$— | H | CH$_3$ | CH$_3$ | 6-CH$_3$ | —C(=O)—OCH$_3$ |
| —CH$_2$—C(=N—NHCH$_3$)—CH$_2$— | H | CH$_3$ | CH$_3$ | 6-CH$_3$ | —C(=O)—OCH(CH$_3$)$_2$ |
| —CH$_2$—C(=N—NH—C$_6$H$_5$)—CH$_2$— | H | CH$_3$ | CH$_3$ | 6-CH$_3$ | H |
| —CH$_2$—C(=N—NH—C$_6$H$_5$)—CH$_2$— | H | CH$_3$ | CH$_3$ | 6-CH$_3$ | —COCH$_3$ |
| —CH$_2$—C(=N—NH—C$_6$H$_5$)—CH$_2$— | H | CH$_3$ | CH$_3$ | 6-CH$_3$ | —CO—C(CH$_3$)$_3$ |
| —CH$_2$—C(=N—NH—C$_6$H$_5$)—CH$_2$— | H | CH$_3$ | CH$_3$ | 6-CH$_3$ | —C(=O)—OCH$_3$ |
| —CH$_2$—C(=N—NH—C$_6$H$_5$)—CH$_2$— | H | CH$_3$ | CH$_3$ | 6-CH$_3$ | —C(=O)—OCH(CH$_3$)$_2$ |
| —CH$_2$—C(=N—N(CH$_3$)$_2$)—CH$_2$— | H | CH$_3$ | CH$_3$ | 6-CH$_3$ | H |
| —CH$_2$—C(=N—N(CH$_3$)$_2$)—CH$_2$— | H | CH$_3$ | CH$_3$ | 6-CH$_3$ | —COCH$_3$ |
| —CH$_2$—C(=N—N(CH$_3$)$_2$)—CH$_2$— | H | CH$_3$ | CH$_3$ | 6-CH$_3$ | —COC(CH$_3$)$_3$ |

TABLE 1-continued

| A | Q | B | X | Y | $Z_n$ | G |
|---|---|---|---|---|---|---|
| $-CH_2-C(=N-N(CH_3)_2)-CH_2-$ | | H | $CH_3$ | $CH_3$ | 6-$CH_3$ | $-C(=O)-OCH_3$ |
| $-CH_2-C(=N-N(CH_3)_2)-CH_2-$ | | H | $CH_3$ | $CH_3$ | 6-$CH_3$ | $-C(=O)-OCH(CH_3)_2$ |
| $-CH_2-C(=N-OH)-CH_2-$ | | H | $CH_3$ | $CH_3$ | 6-$CH_3$ | H |
| $-CH_2-C(=N-OH)-CH_2-$ | | H | $CH_3$ | $CH_3$ | 6-$CH_3$ | $-COCH_3$ |
| $-CH-C(=NOH)-CH_2-$ | | H | $CH_3$ | $CH_3$ | 6-$CH_3$ | $-COC(CH_3)_3$ |
| $-CH_2-C(=N-OH)-CH_2-$ | | H | $CH_3$ | $CH_3$ | 6-$CH_3$ | $-C(=O)-OCH_3$ |
| $-CH_2-C(=N-OH)-CH_2-$ | | H | $CH_3$ | $CH_3$ | 6-$CH_3$ | $-C(=O)-OCH(CH_3)_2$ |
| $-CH_2-C(=N-OCH_3)-CH_2-$ | | H | $CH_3$ | $CH_3$ | 6-$CH_3$ | H |
| $-CH_2-C(=N-OCH_3)-CH_2-$ | | H | $CH_3$ | $CH_3$ | 6-$CH_3$ | $-COCH_3$ |
| $-CH_2-C(=N-OCH_3)-CH_2-$ | | H | $CH_3$ | $CH_3$ | 6-$CH_3$ | $-COC(CH_3)_3$ |
| $-CH_2-C(=N-OCH_3)-CH_2-$ | | H | $CH_3$ | $CH_3$ | 6-$CH_3$ | $-C(=O)-OCH_3$ |
| $-CH_2-C(=N-OCH_3)-CH_2-$ | | H | $CH_3$ | $CH_3$ | 6-$CH_3$ | $-C(=O)-OCH(CH_3)_2$ |
| $-CH_2-C(=N-OC_2H_5)-CH_2-$ | | H | $CH_3$ | $CH_3$ | 6-$CH_3$ | H |
| $-CH_2-C(=N-OC_2H_5)-CH_2-$ | | H | $CH_3$ | $CH_3$ | 6-$CH_3$ | $-COCH_3$ |
| $-CH_2-C(=N-OC_2H_5)-CH_2-$ | | H | $CH_3$ | $CH_3$ | 6-$CH_3$ | $-COC(CH_3)_3$ |
| $-CH_2-C(=N-OC_2H_5)-CH_2-$ | | H | $CH_3$ | $CH_3$ | 6-$CH_3$ | $-C(=O)-OCH_3$ |
| $-CH_2-C(=N-OC_2H_5)-CH_2-$ | | H | $CH_3$ | $CH_3$ | 6-$CH_3$ | $-C(=O)-OCH(CH_3)_2$ |
| $-CH_2-C(=N-OCH(CH_3)_2)-CH_2-$ | | H | $CH_3$ | $CH_3$ | 6-$CH_3$ | H |
| $-CH_2-C(=N-OCH(CH_3)_2)-CH_2-$ | | H | $CH_3$ | $CH_3$ | 6-$CH_3$ | $-COCH_3$ |
| $-CH_2-C(=N-OCH(CH_3)_2)-CH_2-$ | | H | $CH_3$ | $CH_3$ | 6-$CH_3$ | $-COC(CH_3)_3$ |
| $-CH_2-C(=N-OCH(CH_3)_2)-CH_2-$ | | H | $CH_3$ | $CH_3$ | 6-$CH_3$ | $-C(=O)-OCH_3$ |

TABLE 1-continued

| A Q | B | X | Y | $Z_n$ | G |
|---|---|---|---|---|---|
| —CH$_2$—C(=N—OCH(CH$_3$)$_2$)—CH$_2$— | H | CH$_3$ | CH$_3$ | 6-CH$_3$ | —C(=O)—OCH(CH$_3$)$_2$ |
| —CH$_2$—C(=N—O—CH$_2$—C$_6$H$_5$)—CH$_2$— | H | CH$_3$ | CH$_3$ | 6-CH$_3$ | H |
| —CH$_2$—C(=N—O—CH$_2$—C$_6$H$_5$)—CH$_2$— | H | CH$_3$ | CH$_3$ | 6-CH$_3$ | —COCH$_3$ |
| —CH$_2$—C(=N—O—CH$_2$—C$_6$H$_5$)—CH$_2$— | H | CH$_3$ | CH$_3$ | 6-CH$_3$ | —COC(CH$_3$)$_3$ |
| —CH$_2$—C(=N—O—CH$_2$—C$_6$H$_5$)—CH$_2$— | H | CH$_3$ | CH$_3$ | 6-CH$_3$ | —C(=O)—OCH$_3$ |
| —CH$_2$—C(=N—O—CH$_2$—C$_6$H$_5$)—CH$_2$— | H | CH$_3$ | CH$_3$ | 6-CH$_3$ | —C(=O)—OCH(CH$_3$)$_2$ |

If, according to Process (A), ethyl N-(2,6-dichlorophenylacetyl)-6-methyl-piperidine-2-carboxylate is used, the course of the process according to the invention can be illustrated by the following equation:

If, according to Process (A-β), 3-(2,4,6-trimethylphenyl)-1-aza-7-hydroxy-bicyclo-(3,3,0$^{1.5}$)-octane-2,4-dione, oxalyl chloride and a mixture of dimethyl sulphoxide/dichloromethane are used, the course of the process according to the invention can be illustrated by the following equation:

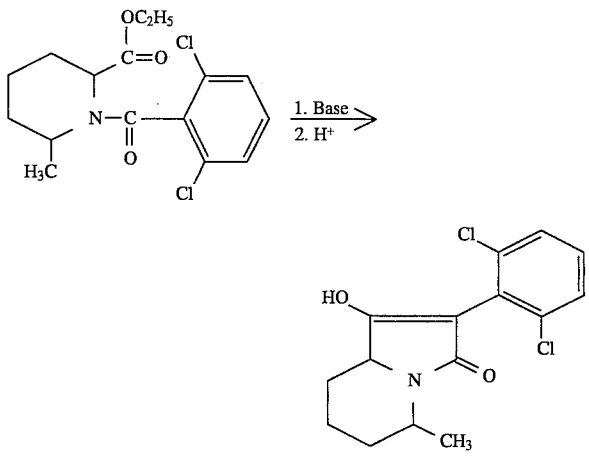

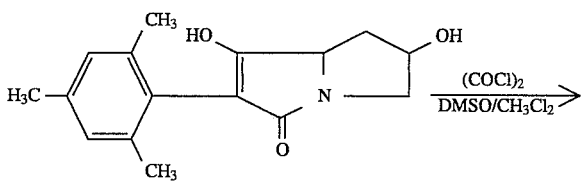

If, according to Process (A-β), 3-(2,4,6-trimethylphenyl)-1-aza-7-hydroxy-bicyclo-(3,3,0$^{1.5}$)-octane-2,4-dione and hydrogen bromide in glacial acetic acid are used, the course of the process according to the invention can be illustrated by the following equation:

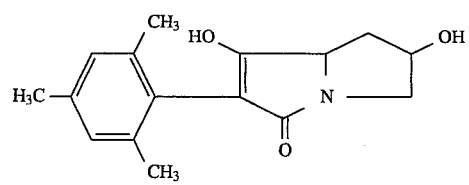

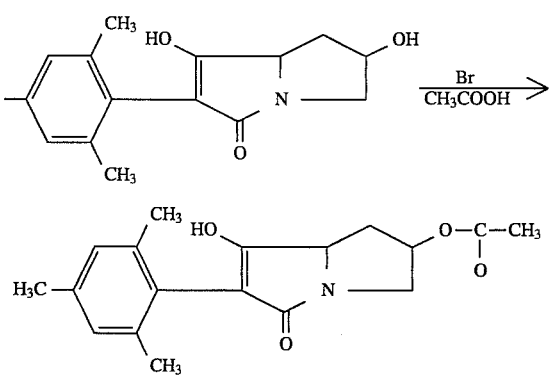

If, according to Process (B) (Variant α), 3-(2,4,6-trimethylphenyl)-1-aza-7,8-dimethyl-bicyclo-(3,3,0$^{1.5}$)-octane-2,4-dione and pivaloyl chloride are used as starting substance, the course of the process according to the invention can be illustrated by the following equation.

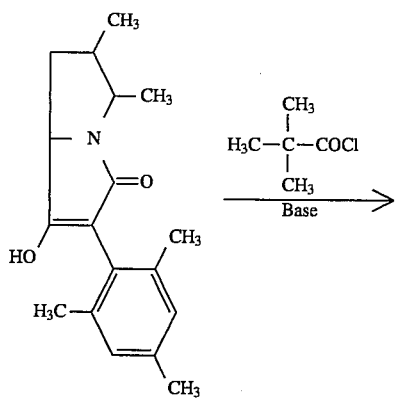

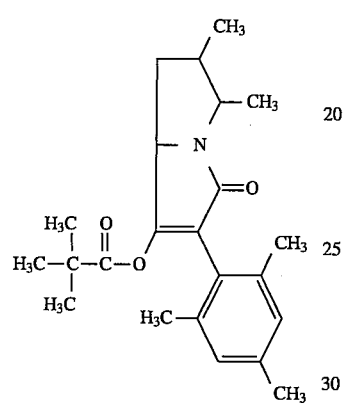

If, according to Process B (Variant β), 8-(2,4,5-trimethylphenyl)-1-aza-3-methyl-bicyclo-(4,3,0$^{1.6}$)-nonane-7,9-dione and acetic anhydride are used as starting compounds, the course of the process according to the invention can be illustrated by the following equation.

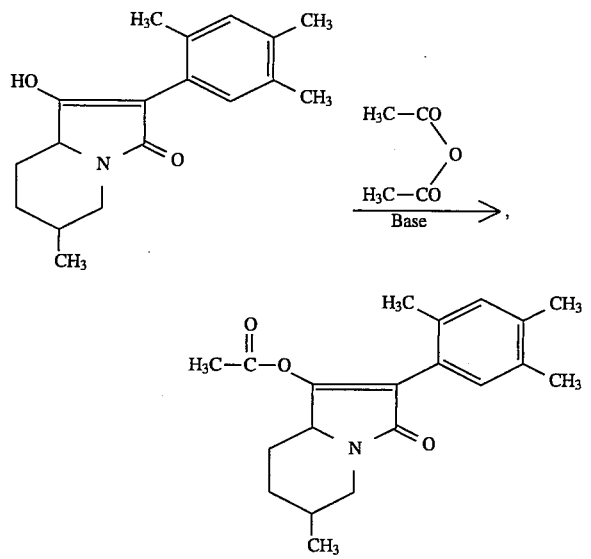

If, according to Process C, 8-(2,4-dichlorophenyl)-1-aza-2-methyl-bicyclo-(4,3,0$^{1.6}$)-nonane-7,9-dione and ethoxyethyl chloroformate are used as starting compounds, the course of the process according to the invention can be illustrated by the following equation.

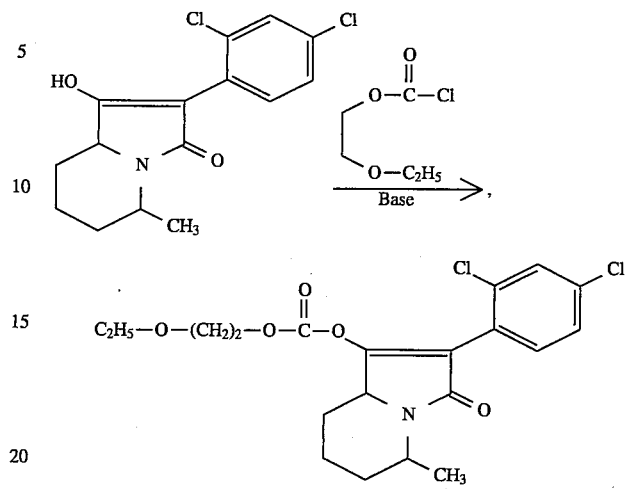

If, according to Process (D$_\alpha$), 3-(2,4,6-trimethylphenyl)-1-aza-7-methoxy-bicyclo-(3,3,0$^{1.5}$)-octane-2,4-dione and methyl chloromonothioformate are used as starting materials, the course of the reaction can be illustrated as follows:

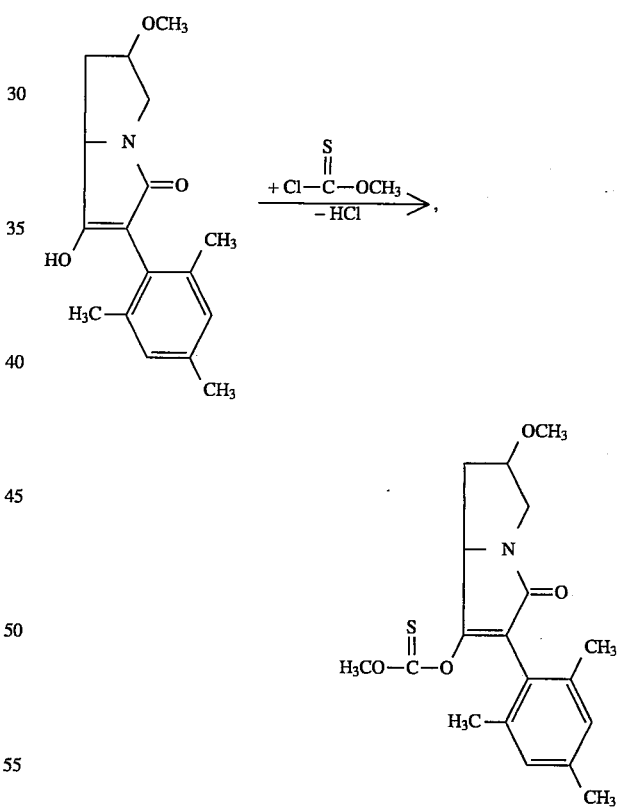

If, according to Process (D$_\alpha$), 3-(2,4,6-trimethylphenyl)-1-aza-7,8-dimethyl-bicyclo-(3,3,0$^{1.5}$)-octane-2,4-dione, carbon disulphide and methyl iodide are used as starting components, the course of the reaction can be illustrated as follows:

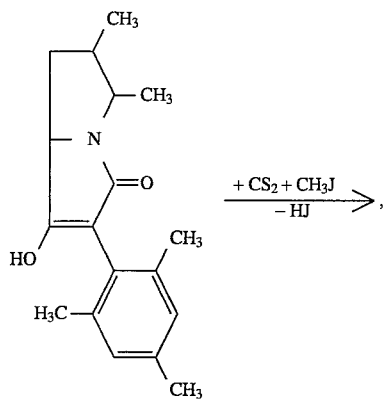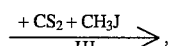

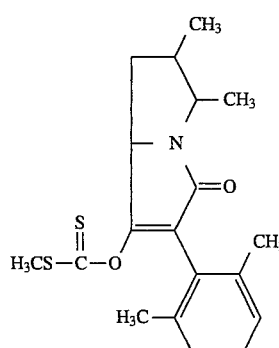

If, according to Process (E), 3-(2,4,6-trimethylphenyl)-1-aza-7-isopropyl-bicyclo-(3,3,0¹·⁵)-nonane-2,4-dione and methanesulphonyl chloride are used as starting material, the course of the reaction can be illustrated by the following equation:

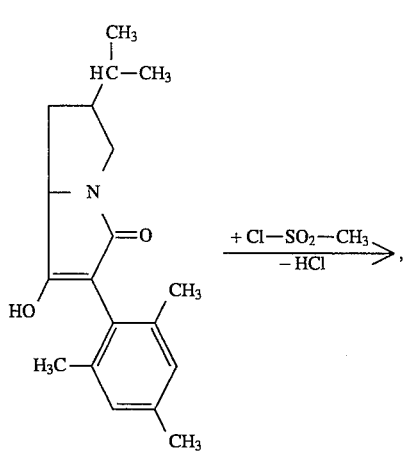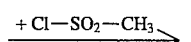

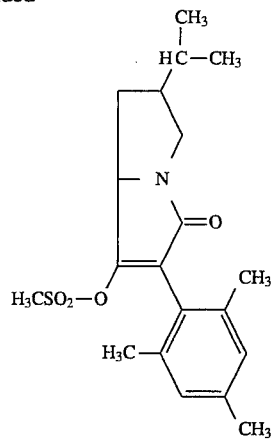

If, according to Process (F), 3-(2,4,6-trimethylphenyl)-1-aza-6,8-dimethyl-bicyclo-(3,3,0¹·⁵)-octane-2,4-dione and the 2,2,2-trifluoroethyl ester of methanethio-phosphonyl chloride are used as starting materials, the course of the reaction can be illustrated by the following equation:

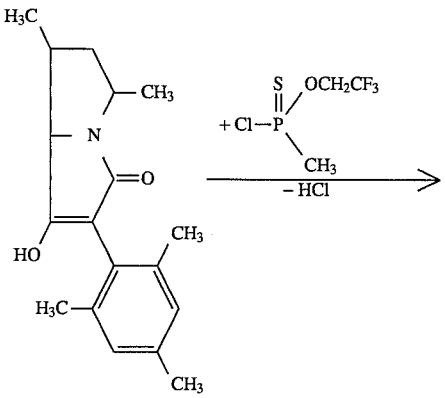

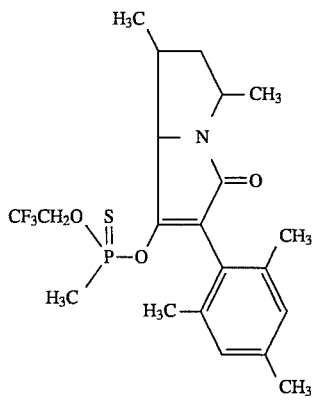

If, according to Process (G), 3-(2,4,6-trimethylphenyl)-1-aza-7,8-dimethyl-bicyclo-(3,3,0¹·⁵)-octane-2,4-dione and NaOH are used as components, the course of the process according to the invention can be illustrated by the following equation:

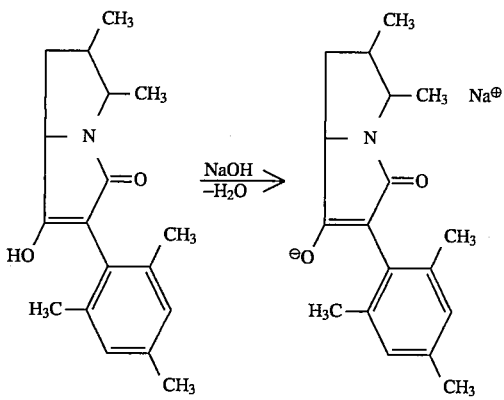

Formula (II) provides a general definition of the N-acylamino acid esters required as starting substances for carrying out Process (A) according to the invention. In this formula (II), A, B, Q, X, Y, Z, n and $R^{10}$ preferably represent those radicals which have already been mentioned in connection with the description of the substances of the formula (I) according to the invention as being preferred for these substituents.

The compounds of the formula (II) are known in some cases (cf., for example, EP-A 355,599, DE-A 3,831,852 and J. Heterocycl. Chem. 25 (1), 49–57). The compounds which were hitherto unknown, however, can be prepared analogously in a simple manner by methods known in principle. For example, acyl-amino acid esters of the formula (II) are obtained when a) amino acid esters of the formula (XII)

in which $R^{10-1}$ represents hydrogen (XIIa) or alkyl (XIIb) and

A, B and Q have the abovementioned meaning, are acrylated with phenylacetyl halides of the formula (XIII)

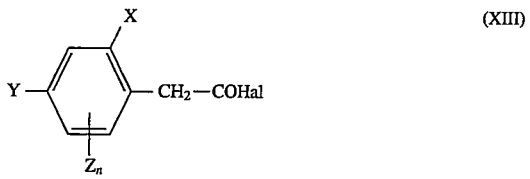

in which

X, Y, Z and n have the abovementioned meaning and

Hal represents chlorine or bromine (Chem. Reviews 52 237–416 (1953)); or b) when acylamino acids of the formula (IIa)

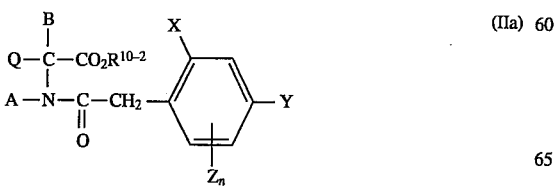

in which

A, B, Q, X, Y, z and n have the abovementioned meaning and $R^{10-2}$ represents hydrogen are esterified (Chem. Ind. (London) 1568 (1968)).

Compounds of the formula (XII) in which

A, B and $R^{10-1}$ have the abovementioned meaning, are known or can be obtained by processes known from the literature (Henning, R., Urbach, H., Tetrahedron Lett. 24, 5339–5342 (1983); EP-A 52,870; U.S. Pat. No. 4,291,163; EP-A 173,199; Urbach, H., Henning, R., Tetrahedron Lett. 26, 1839–1842 (1985).

The phenylacetyl halides of the formula (XIII) are generally known compounds of organic chemistry. Formula (IIa) provides a general definition of the acylamino acids required for preparing the acyl-amino acid esters of the formula (II). In this formula (IIa), A, B, Q, X, Y, Z and n preferably represent those radicals which have already been mentioned in connection with the description of the substances of the formula (I) according to the invention as being preferred for these substituents. $R^{10-2}$ represents hydrogen.

The compounds of the formula (IIa) are known in some cases (cf., for example, EP-OS (European Published Specification) 355,599 and J. Am. Chem. Soc. 110 (4), 1180–6). The compounds which were hitherto unknown, however, can be prepared analogously in a simple manner by methods known in principle.

For example, the compounds of the formula (IIa) can be obtained from the phenylacetyl halides of the formula (XIII) and amino acids of the formula (XIIa) by the method of Schotten-Baumann (Organikum [Laboratory Practical of Organic Chemistry], 9th Edition 446 (1970) VEB Deutscher Verlag der Wissenschaften, Berlin).

The following compounds of the formula (II) may be mentioned by way of example but without limitation in addition to the intermediates mentioned in the Preparation Examples:

ethyl N-(2,4-dichlorophenylacetyl)-5-methyl-pyrrolidine-2-carboxytate, ethyl N-(2,6-dichlorophenylacetyl)-5-methyl-pyrrolidine-2-carboxylate, ethyl N-(2,4,6-trichlorophenylacetyl-5-methyl-pyrrolidine-2-carboxylate, ethyl N-(2,4-dimethylphenylacetyl)-5-methyl-pyrrolidine-2-carboxylate, ethyl N-(2,6-dimethylphenylacetyl)-5-methyl-pyrrolidine-2-carboxylate, ethyl N-(2,4,6-trimethylphenylacetyl)-5-methyl-pyrrolidine-2-carboxylate, ethyl N-(2,4-dichlorophenylacetyl)-4-methyl-pyrrolidine-2-carboxylate, ethyl N-(2,6-dichlorophenylacetyl)-4-methyl-pyrrolidine-2-carboxylate, ethyl N-(2,4,6-trichlorophenyiacetyl)-4-methyl-pyrrolidinc-2-carboxylate, ethyl N-(2,4-dimethylphenylacetyl)-4-methyl-pyrrolidine-2-carboxylate, ethyl N-(2,6-dimethylphenylacetyl)-4-methyl-pyrrolidine-2-carboxylate, ethyl N-(2,4,6-trimethylphenylacetyl)-4-methyl-pyrrolidine-2-carboxylate, ethyl N-(2,4-dichlorophenlacetyl)-3-methyl-pyrrolidine-2-carboxylate, ethyl N-(2,6-dichlorophenylacetyl)-3-methyl-pyrrolidine-2-carboxylate, ethyl N-(2,4,6-trichlorophenylacetyl)-3-methyl-pyrrolidine-2-carboxylate, ethyl N-(2,4-dimethylphenylacetyl)-3-methyl-pyrrolidine-2-carboxylate, ethyl N-(2,6-dimethylphenylacetyl)-3-methyl-pyrrolidine-2-carboxylate, ethyl N-(2,4,6-trimethylphenylacetyl)-3-methyl-pyrrolidine-2-carboxylate, ethyl N-(2,4-dichlorophenylacetyl)-2-methyl-pyrrolidine-2-carboxylate, ethyl N-(2,6-dichlorophenylacetyl)-2-methyl-pyrrolidine-2-carboxylate, ethyl N-(2,4,6-trichlorophenylacetyl)-2-methyl-pyrrolidine-2- carboxylate, ethyl N-(2,4-dimethylphenylacetyl)-2-methyl-pyrrolidine-2-carboxylate, ethyl N-(2,6-dimethylphenylacetyl)-2-methyl-pyrrolidine-2-carboxylate, ethyl N-(2,4,6-trimethylphenylacetyl)-2-methyl-pyrrolidine-2-carboxylate, ethyl N-(2,4-dichlorophenylacetyl)-4,5-dimethyl-pyrrolidine-2-carboxylate, ethyl N-(2,6-dichlorophenylacetyl)-4,5-dimethyl-pyrrolidine-2-carboxylate, ethyl N-(2,4,6-trichlorophenylacetyl)-4,5-dimethyl-pyrrolidine-2-carboxylate, ethyl N-(2,4-dimethylphenylacetyl)-4,5-dimethyl-pyrrolidine-2-carboxylate, ethyl N-(2,6-dimethylphenylacetyl)-4,5-dimethyl-pyrrolidine-2-carboxylate, ethyl N-(2,4,6-trimethylphenylacetyl)-4,5-dimethyl-pyrrolidine-2-carboxylate, ethyl N-(2,4-dichlorophenylacetyl)-3,5-dimethylpyrrolidine-2-carboxylate, ethyl N-(2,6-dichlorophenylacetyl)-3,5-dimethyl-pyrrolidine-2-carboxylate, ethyl N-(2,4,6-trichlorophenylacetyl)-3,5-dimethylpyrrolidine-2-carboxylate, ethyl N-(2,4-dimethylphenylacetyl)-3,5-dimethyl-pyrrolidine-2-carboxylate, ethyl N-(2,6-dimethylphenylacetyl)-3,5-dimethyl-pyrrolidine-2-carboxylate, ethyl N-(2,4-6-trimethylphenylacetyl)-3,5-dimethyl-pyrrolidine-2-carboxylate, ethyl N-(2,4-dichlorophenylacetyl)-3,4,5-trimethyl-pyrrolidine-2-carboxylate, ethyl N-(2,6-dichlorophenylacetyl)-3,4,5-trimethyl-pyrrolidine-2-carboxylate, ethyl N-(2,4,6-trichlorophenylacetyl)-3,4,5-trimethyl-pyrrolidine-2-carboxylate, ethyl N-(2,4-dimethylphenylacetyl)-3,4,5-trimethyl-pyrrolidine-2-carboxylate, ethyl N-(2,6-dimethylphenylacetyl)-3,4,5-trimethyl-pyrrolidine-2-carboxylate, ethyl N-(2,4,6-trimethylphenylacetyl)-3,4,5-trimethyl-pyrrolidine-2-carboxylate, ethyl N-(2,4-dichlorophenylacetyl)-5-cyclohexyl-pyrrolidine-2-carboxylate, ethyl N-(2,6-dichlorophenylacetyl)-5-cyclohexylpyrrolidine-2-carboxylate, ethyl N-(2,4,6-trichlorophenylacetyl)-5-cyclohexyl-pyrrolidine-2-carboxylate, ethyl N-(2,4-dimethylphenylacetyl)-5-cyclohexylpyrrolidine-2-carboxylate, ethyl N-(2,6-dimethylphenylacetyl)-5-cyclohexyl-pyrrolidine-2-carboxylate, ethyl N-(2,4,6-trimethylphenylacetyl)-5-cyclohexylpyrrolidine-2-carboxylate, ethyl N-(2,4-dichlorophenylacetyl)-4-hydroxy-pyrrolidine-2-carboxylate, ethyl N-(2,6-dichlorophenylacetyl)-4-hydroxy-pyrrolidine-2-carboxylate, ethyl N-(2,4,6-trichlorophenylacetyl)-4-hydroxy-pyrrolidine-2-carboxylate, ethyl N-(2,4-dimethylphenylacetyl)-4-hydroxy-pyrrolidine-2-carboxylate, ethyl N-(2,6-dimethylphenylacetyl)-4-hydroxy-pyrrolidine-2-carboxylate, ethyl N-(2,4,6-trimethylphenylacetyl)-4-hydroxy-pyrrolidine-2-carboxylate, ethyl N-(2,4-dichlorophenylacetyl)-4-methoxy-pyrrolidine-2-carboxylate, ethyl N-(2,6-dichlorophenylacetyl)-4-methoxy-pyrrolidine-2-carboxylate, ethyl N-(2,4,6-trichlorophenylacetyl)-4-methoxy-pyrrolidine-2-carboxylate, ethyl N-(2,4-dimethylphenylacetyl)-4-methoxy-pyrrolidine-2-carboxylate, ethyl N-(2,6-dimethylphenylacetyl)-4-methoxy-pyrrolidine-2-carboxylate, ethyl N-(2,4,6-trimethylphenylacetyl)-4-methoxy-pyrrolidine-2-carboxylate, ethyl N-(2,4-dichlorophenylacetyl)-3-methyl-piperidine-2-carboxylate, ethyl N-(2,6-dichlorophenylacetyl)-3-methyl-piperidine-2-carboxylate, ethyl N-(2,4,6-trichlorophenylacetyl)-3-methyl-piperidine-2-carboxylate, ethyl N-(2,4-dimethylphenylacetyl)-3-methyl-piperidine-2-carboxylate, ethyl N-(2,6-dimethylphenylacetyl)-3-methyl-piperidine-2-carboxylate, ethyl N-(2,4,6-trimethylphenylacetyl)-3-methyl-piperidine-2-carboxylate, ethyl N-(2,4-dichlorophenylacetyl)-4-methyl-piperidine-2-carboxylate, ethyl N-(2,6-dichlorophenylacetyl)-4-methyl-piperidine-2-carboxylate, ethyl N-(2,4,6-trichlorophenylacetyl)-4-methyl-piperidine-2-carboxylate, ethyl N-(2,4-dimethylphenylacetyl)-4-methyl-piperidine-2-carboxylate, ethyl N-(2,6-dimethylphenylacetyl)-4-methyl-piperidine-2-carboxylate, ethyl N-(2,4,6-trimethylphenylacetyl)-4-methyl-piperidine-2-carboxylate, ethyl N-(2,4-dichlorophenylacetyl)-5-methyl-piperidine-2-carboxylate, ethyl N-(2,6-dichlorophenylacetyl)-5-methyl-piperidine-2-carboxylate, ethyl N-(2,4,6-trichlorophenylacetyl)-5-methyl-piperidine-2-carborylate, ethyl N-(2,4-dimethylphenylacetyl)-5-methyl-piperidine-2-carboxylate, ethyl N-(2,6-dimethylphenylacetyl)-5-methyl-piperidine-2-carboxylate, ethyl N-(2,4,6-trimethylphenylacetyl)-5-methyl-piperidine-2-carboxylate, ethyl N-(2,4-dichlorophenylacetyl)-6-methyl-piperidine-2-carboxylate, ethyl N-(2,6-dichlorophenylacetyl)-6-methylpiperidine-2-carboxylate, ethyl N-(2,4,6-trichlorophenylacetyl)-6-methyl-piperidine-2-carboxylate, ethyl N-(2,4-dimethylphenylacetyl)-6-methyl-piperidine-2-carboxylate, ethyl N-(2,6-dimethylphenylacetyl)-6-methyl-piperidine-2-carboxylate, ethyl N-(2,4,6-trimethylphenylacetyl)-6-methyl-piperidine-2-carboxylate, ethyl N-(2,4-dichlorophenylacetyl)-4,6-dimethyl-piperidine-2-carboxylate, ethyl N-(2,6-dichlorophenylacetyl)-4,6-dimethyl-piperidine-2-carboxylate, ethyl N-(2,4,6-trichlorophenylacetyl)-4,6-dimethyl-piperidine-2-carboxylate, ethyl N-(2,4-dimethylphenylacetyl)-4,6-dimethyl-piperidine-2-carboxylate, ethyl N-(2,6-dimethylphenylacetyl)-4,6-dimethyl-piperidine-2-carboxylate and ethyl N-(2,4,6-trimethylphenylacetyl)-4,6-dimethyl-piperidine-2-carboxylate.

Formula (Ia) provides a general definition of the 3-aryl-pyrrolidone-2,4-diones or enols thereof which are required as starting substances for carrying out Processes (B), (C), (D), (E), (F) and (G) according to the invention. In this formula (Ia), A, B, Q, X, Y, Z and n preferably represent those radicals which have already been mentioned in connection with the description of the substances of the formula (I) according to the invention as being preferred for these substituents.

The compounds of the formula (Ia) are new and the subject of the present invention. They can be obtained by Process (A).

The acid halides of the formula (III), carboxylate anhydrides of the formula (IV), chloroformic acid esters or chloroformic acid thioesters of the formula (V), chloromonothioformic acid esters or chlorodithioformic acid esters of the formula (VI), alkyl halides of the formula (VII), sulphonyl chlorides of the formula (VIII), phosphorus compounds of the formula (IX) and metal hydroxides or amines of the formula (X) and (XI), which are furthermore required as starting substances for carrying out Processes (B), (C), (D), (E), (F) and (G) according to the invention, are generally known compounds of organic or inorganic chemistry.

Process (A α) is characterised in that compounds of the formula (II) in which A, X, Y, Z, n and $R^{10}$ have the abovementioned meaning are subjected to an intramolecular condensation reaction in the presence of bases.

Diluents which can be employed in Process (A α) according to the invention are all inert organic solvents. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide and N-methyl-pyrrolidone, and also alcohols such as methanol, ethanol, propanol, isopropanol, butanol, iso-butanol and tert.-butanol.

Bases (deprotonating agents) which can be employed when carrying out Process (A α) according to the invention are all customary proton acceptors. The following can preferably be used: oxides, hydroxides and carbonates of alkali metals and alkaline earth metals, such as sodium hydroxide, potassium hydroxide, magnesium oxide, calcium oxide, sodium carbonate, potassium carbonate and calcium carbonate, sodium carbonate, potassium carbonate and calcium carbonate, all of which can also be employed in the presence of phase-transfer catalysts such as, for example, triethylbenzylanunonium chloride, tetrabutylammonium bromide, Adogen 464 or TDA 1. Furthermore, alkali metals such as sodium or potassium can be used. Moreover, amides and hydrides of alkali metals and alkaline earth metals such as sodium amide, sodium hydride and calcium hydride, and in addition also alkali metal alcoholates such as sodium methylate, sodium ethylate and potassium tert.-butylate, can also be employed.

Adogen 464=methyltrialkyl($C_8$–$C_{10}$)ammonium chloride
TDA 1=tris-(methoxyethoxyethyl)-amine When carrying out Process (A α) according to the invention, the reaction temperatures can be varied within a substantial range. In general, the process is carried out at temperatures between 0° C. and 250° C., preferably between 50° C. and 150° C.

Processes (A α), and (A β) according to the invention are generally carried out under atmospheric pressure.

When carrying out Proces (A α) according to the invention, the reactants of the formulae (II) and the deprotonating bases are generally employed in approximately equimolar amounts. However, it is also possible to use one or the other components in a larger excess (up to 3 mol).

The reactions of the hydroxy group according to the process (A β) to obtain the corresponding esters and ethers, the Swern oxidation or the Pfitzner-Moffart oxidation as well as the reaction of the resulting ketones with amines, alcohols, dioles, mercaptanes and dithioles are carried out according to generally known methods (compare for example with Organikum, VEB Deutscher Verlag der Wissenschaften, Berlin 1976 and the preparation examples).

Process (Bα) is characterised in that compounds of the formula (Ia) are reacted with carboxylic acid halides of the formula (III).

When carrying out Process (Bα) according to the invention using the acid halides, the diluents which can be employed are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic acid esters such as ethyl acetate, and also strongly polar solvents such as dimethyl sulphoxide and sulpholane. If the acid halide is sufficiently hydrolysis-stable, the reaction can also be carried out in the presence of water.

If the corresponding carboxylic acid halides are used, then suitable acid-binding agents in the conversion by Process (Bα) according to the invention are all customary acid acceptors. The following can preferably be used: amines such as triethylamine, pyridine, diazabicyclooctane (DABCO), diazabicycloundecane (DBU), diazabicyclononene (DBN), Hüning base and N,N-dimethyl-aniline, furthermore alkaline earth metal oxides such as magnesium oxide and calcium oxide, and additionally alkali metal carbonates and alkaline earth metal carbonates such as sodium carbonate, potassium carbonate and calcium carbonate.

When carboxylic acid halides are used, the reaction temperatures in Process (Bα) according to the invention can also be varied within a substantial range. In general, the process is carried out a temperature between –20° C. and +150° C., preferably between 0° C. and 100° C.

When carrying out Process (Bα) according to the invention, the starting substances of the formula (Ia) and the carboxylic halide of the formula (III) are generally used in approximately equivalent amounts. However, it is also possible to employ the carboxylic anhydride in a larger excess (up to 5 mol). Working-up is carried out by customary methods.

Process (Bβ) is characterised in that compounds of the formula (Ia) are reacted with carboxylic hydrides of the formula (IV).

If, in Process (Bβ) according to the invention, carboxylic anhydrides are used as the reactant of the formula (IV), then the diluents which can be used are preferably those diluents which are also preferably suitable when acid Halides are used. Besides, an excess of carboxylic hydride employed can also simultaneously act as the diluent.

When carboxylic anhydrides are used, the reaction temperatures in Process (Bβ) according to the invention can also be varied within a substantial range. In general, the reaction is carried out at temperatures between –20° C. and +150° C., preferably between 0° C. and 100° C.

When carrying out the process according to the invention, the starting substances of the formula (Ia) and the carboxylic anhydride of the formula (IV) are generally used in approximately equivalent amounts. However, it is also possible to employ the carboxylic anhydride in a larger excess (up to 5 mol). Working-up is carried out by customary methods.

In general, a procedure is followed in which diluent and excess carboxylic anhydride as well as the carboxylic acid which forms are removed by distillation or by washing with an organic solvent or with water.

Process (C) is characterised in that compounds of the formula (Ia) are reacted with chloroformic acid esters or chloroformic acid thioesters of the formula (V).

If the corresponding chloroformic acid esters or chloroformic acid thioesters are used, then acid-binding agents which are suitable for the reaction by Process (C) according to the invention are all customary acid acceptors. The following can preferably be used: tertiary amines such as triethylamine, pyridine, DABCO, DBU, DBA, Hünig base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate.

Diluents which can be employed in Process (C) according to the invention when the chloroformic acid esters or chloroformic acid thioesters are used are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic acid esters such as ethyl acetate, and also strongly polar solvents such as dimethyl sulphoxide and sulpholane.

When using the chloroformic acid esters or chloroformic acid thioesters as the carboxylic acid derivatives of the formula (V), the reaction temperatures when carrying out Process (C) according to the invention can be varied within a substantial range. If the process is carried out in the presence of a diluent and of an acid-binding agent, then the reaction temperatures are generally between −20° C. and +100° C., preferably between 0° C. and 50° C.

Process (C) according to the invention is generally carried out under atmospheric pressure.

When carrying out Process (C) according to the invention, the starting substances of the formula (Ia) and the corresponding chloroformic acid ester or chloroformic acid thioester of the formula (V) are generally used in approximately equivalent amounts. However, it is also possible to employ one or the other component in a larger excess (up to 2 mol). Working-up is then carried out by customary methods. In general, a procedure is followed in which precipitated salts are removed and the reaction mixture which remains is concentrated by stripping off the diluent.

In Preparation Process ($D_\alpha$), approximately 1 mole of chloromonothioformic acid ester or chlorodithioformic acid ester of the formula (VI) is reacted per mole of starting compound of the formula (Ia) at 0° to 120° C., preferably at 20° to 60° C.

Suitable diluents which may be added are all inert polar organic solvents such as ethers, amides, alcohols, sulphones and sulphoxides.

Dimethyl sulphoxide, tetrahydrofuran, dimethylformamide and dimethyl sulphide are preferably employed.

If, in a preferred embodiment, the enolate salt of the Compound Ia is synthesized by adding strong deprotonating agents such as, for example sodium hydride or potassium tertiary butylate, a further addition of acid-binding agents can be dispensed with.

If acid-binding agents are employed, then customary inorganic or organic bases are suitable, examples which may be mentioned being sodium hydroxide, sodium carbonate, potassium carbonate, pyridine and triethylamine.

The reaction can be carried out under atmospheric pressure or under increased pressure, it is preferably carried out under atmospheric pressure. Working-up is effected by customary methods.

In Preparation Process ($D_\beta$), the equimolar amount, or an excess, of carbon disulphide is added per mole of starting compound of the formula (Ia). This process is preferably carried out at temperatures from 0° to 50° C. and, in particular, at 20° to 30° C.

It is often expedient to first prepare the corresponding salt from the compound of the formula (Ia) by adding a deprotonating agent (such as, for example, potassium tertiary butylate or sodium hydride). The Compound (Ia) is reacted with carbon disulphide until the formation of the intermediate is complete, for example after stirring for several hours at room temperature.

The further reaction with the alkyl halide of the formula (VII) is preferably carried out at 0° to 70° C. and, in particular at 20° to 50° C. In this process, at least the equimolar amount of alkyl halide is employed.

The process is carried out under atmospheric pressure or under increased pressure, preferably under atmospheric pressure.

Again, working-up is effected by customary methods.

In Preparation Process (E), approx. 1 mol of sulphonyl chloride (VIII) is reacted per mole of starting compound of the formula (Ia) at 0° to 150° C., preferably at 20° to 70° C.

Suitable diluents which may be added are all inert polar organic solvents such as ethers, amides, nitriles, alcohols, sulphones or sulphoxides.

Dimethyl sulphoxide, tetrahydrofuran, dimethylformamide and dimethyl sulphide are preferably employed.

If, in a preferred embodiment, the enolate salt of the Compound Ia is synthesised by adding strong deprotonating agents (such as, for example, sodium hydride or potassium tertiary butylate), a further addition of acid-binding agents can be dispensed with.

If acid-binding agents are employed, then customary inorganic or organic bases are suitable, examples which may be mentioned being sodium hydroxide, sodium carbonate, potassium carbonate and pyridine.

The reaction can be carried out under atmospheric pressure or under increased pressure, it is preferably carried out under atmospheric pressure. Working-up is effected by customary methods.

If appropriate, Preparation Process (E) can be carried out under phase-transfer conditions (W. J. Spillane et al.; J. Chem. Soc., Perkin Trans I, (3) 677–9 (1982)). In this case, 0.3 to 1.5 mol of sulphonyl chloride VIII, preferably 0.5 mol, are reacted per mole of starting compound of the formula a) at. 0° to 150° C., preferably at 20° to 70° C.

Phase-transfer catalysts which can be used are all quaternary ammonium salts, preferably tetraoctylammonium bromide and benzyltriethylammonium chloride. Organic solvents which can be used in this case are all unpolar inert solvents, and benzene and toluene are preferably employed.

To obtain compounds of the Structure (Ie) in Preparation Process (F), 1 to 2, preferably 1 to 1.3, mol of the phosphorus compound of the formula (IX) are employed per mole of Compound (Ia) at temperatures between −40° C. and 150° C., preferably between −10° and 110° C.

Suitable diluents which may be added are all inert polar organic solvents such as ethers, amides, nitriles, alcohols, sulphides, sulphones, sulphoxides, etc.

Acetonitrile, dimethyl sulphoxide, tetrahydrofuran, dimethylformamide and dimethyl sulphide are preferably employed.

Suitable acid-binding agents which may be added are customary inorganic or organic bases such as hydroxides or carbonates. Sodium hydroxide, sodium carbonate, potassium carbonate and pyridine may be mentioned by way of example.

The reaction can be carried out under atmospheric pressure or under increased pressure, it is preferably carried out under atmospheric pressure. Working-up is effected by customary methods of organic chemistry. The end products obtained are preferably purified by crystallisation, chromatographic purification or by so-called "incipient distillation", that is to say removal of the volatile components in vacuo.

Process (G) is characterised in that compounds of the formula (Ia) are reacted with metal hydroxides (X) or amines (XI).

Diluents which can be employed in the process according to the invention are preferably ethers such as tetrahydrofuran, dioxane or diethyl ether, but also alcohols such as methanol, ethanol or isopropanol, or even water. In general, Process (H) according to the invention is carried out under atmospheric pressure. In general, the reaction temperatures are between −20° C. and 100° C., preferably between 0° C. and 50° C.

When carrying out Process (G) according to the invention, the starting substances of the formula (Ia) or (X) or (XI) are generally employed in approximately equimolar amounts. However, it is also possible to employ one or the other component in a larger excess (up to 2 mol). In general, a procedure is followed in which the reaction mixture is concentrated by stripping off the diluent.

The active compounds are suitable for combating animal pests, preferably arthropods and nematodes, in particular insects and arachnida, which are encountered in agriculture, in forests, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Antho nomus spp., Sitophilus spp., *Otiorrhynchus sulcatus, Cosmopolites sordidus, Ceuthorrhynchus assimilis, Hypera postica*, Dermistes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Cono derus spp., *Melolontha melolontha, Amphimallon solsti tialis* and *Costelytra zealandica*. From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds according to the invention are distinguished by a high insecticidal and acaricidal activity.

They can be employed with particularly good success for combating insects which damage plants such as, for example, against the larvae of the mustard beetle (*Phaedon cochleariae*) or against the larvae of the green rice cicada (*Nephotettix cincticeps*) for combating mites which damage plants such as, for example, against the greenhouse red spider mite or the two-spotted spider mite (*Tetranychus urticae*).

Furthermore, the active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land and for the selective combating of weeds in annual cultures.

The active compounds according to the invention are very suitable for selectively combating monocotyledon weeds in dicotyledon cultures by the pre- and post-emergence methods. For example, they can be employed with very good success in soya beans, Helianthus (sunflower) or sugar beet for combating grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet, and 4-amino-6-(1,1-dimethylethyl)-3-methylthio-1,2,4-triazin-5(4H)-one (METRIBUZIN) for combating weeds in soya beans. 2,4-Dichlorophenoxyacetic acid (2,4D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-[(4-methoxy-6-methyl-1,3,5-triazin-2-yl)amino]-carbonyl-benzenesulphonamide (CHLORSULFURON); 2-[4-(2,4-dichlorophenoxy)-phenoxy]-propionic acid, its methyl ester or its ethyl ester (DICLOFOPMETHYL); 4-amino-6-t-butyl-3-ethylthio-1,2,4-triazin-5(4H)-one (ETHIOZIN); 2-4-[(6-chloro-2-benzoxazolyl)-oxy]-phenoxy-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl))-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-[[((4-methoxy-6-methyl-1,3,5-triazin-2-yl)amino)-carbonyl]-amino]-sulphonyl-benzoic acid or its methyl ester (METSULFURON); N-(1-ethylpropyl)-3,4-dimethyl-2,6-dinitroaniline (PENDIMETHALIN); O-(6-chloro-3-phenylpyridazin-4-yl) S-octyl thiocarbonate (PYRIDATE); 4-ethylamino-2-t-butylamino-6-methylthio-s-triazine (TERBUTRYNE) and methyl 3-[[[[4-methoxy-6-methyl-1, 3,5-triazin-2-yl)amino]-carbonyl]-amino]-sulphonyl]-thiophene-2-carboxylate (THIAMETURON) are also suitable. Surprisingly, some mixtures also show synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

Preparation Examples

EXAMPLE 1

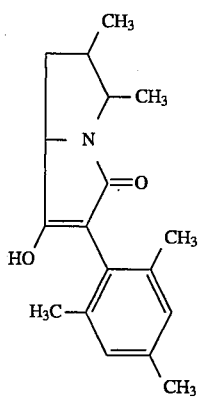

(Process (A))

16 g (0.048 mol) of ethyl N-(2,4,6-trimethylphenyl-acetyl-4,5-dimethyl-pyrrolidine-2-carboxylate in 50 ml of absolute toluene are added dropwise to a boiling solution of 2 g (0.067 mol) of NaH in 50 ml of absolute toluene and the mixture is refluxed. The end of the reaction is determined by TLC monitoring. The mixture is subsequently allow to cool to room temperature, and absolute ethanol is added with cooling until hydrogen is no longer evolved. The reaction mixture is evaporated under reduced pressure, the residue is taken up in water, and the mixture is acidified at room temperature using concentrated hydrochloric acid. The precipitate is filtered off with suction and dried in vacuo at 70° C. over $P_2O_5$. Purification is effected by extracting by boiling with chloroform/methyl tert-butyl ether and ether/n-hexane.

6.2 g (45.3%) of theory of 3-(2,4,6-trimethylphenyl)-1-aza-7,8-dimethyl-bicyclo-(3.3.0$^{1.5}$)-octane-2,4-dion of a melting point of >220° C. are obtained.

EXAMPLE 2

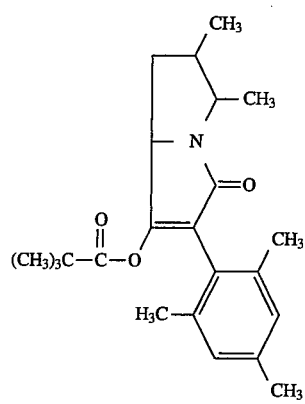

(Process (Bα))

A mixture of 2.3 g (0.008 mol) of 3-(2,4,6-trimethylphenyl)-1-aza-7,8-dimethyl-bicyclo-(3,3,0$^{1.5}$)-octane-2,4-dione and 1.4 ml of ethyldiisopropylamine are cooled to from 0° C. to 10° C., and 1.01 ml of pivaloyl chloride in 5 ml of methyl tert-butyl ether are added dropwise to the mixture. The batch is subsequently stirred at room temperature until the reaction has ended (TLC monitoring). The precipitate which has separated out is then filtered off with suction and washed with methyl tert-butyl ether, and the filtrate is evaporated under reduced pressure.

After purification on silica gel by column chromatography (mobile phase cyclohexane/ethyl acetate 1:1), 2.12 g (71.7% of theory) of 3-(2,4,6-trimethylphenyl)-4-(tert-butylcarbonyloxy)-1-aza-7,8-dimethyl-bicyclo-(3,3,β$^{1.5}$)-octane-2-one of melting point 89° C. are obtained.

EXAMPLE 3

3-(2,4,6-Trimethylphenyl)-4-acetyloxy-1-aza-7,8-dimethyl-bicyclo-(3,3,0$^{1.5}$)-octane-2-one is obtained as an oil in analogy to Example 2.

EXAMPLE 4

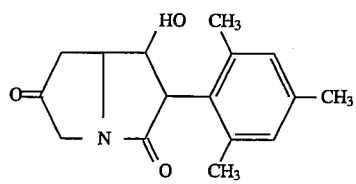

A solution of 34.4 g (0.44 mol) of dimethyl sulphoxide is added dropwise to a solution of 28.0 g (0.22 mol) of oxalyl chloride in 500 ml of absolute dichloromethane at −60° C., stirring is carried out/or 10 minutes and a solution of 54.66 g (0.2 mol) of 3-(2,4,6-trimethylphenyl)-1-sta-7-hydroxy-bicyclo(3,3,0$^{1.5}$)-octane-2,4-dione in 200 ml of absolute dichloromethane/dimethyl sulphoxide (10:1) is added dropwise. Stirring is continued for another 15 minutes, then 101.2 g (1.0 mol) of triethylamine are added, temperature is raised to ambient temperature and 1 l of water is added to the reaction mixture. The organic phase is separated, dried and evaporated at 80° C. in the rotary evaporator. The purification is carried out by flash-chromatography on silica gel by using $CH_2Cl_2/CH_3OH$ 20:1.

50.56 g (93% of theory) of 3-(2,4,6-trimethylphenyl)-1-aza-7-hydroxy-bicyclo(3,3,0$^{1.5}$)-octane-2,4-dione having a melting point of 240° C. are obtained.

EXAMPLE 5

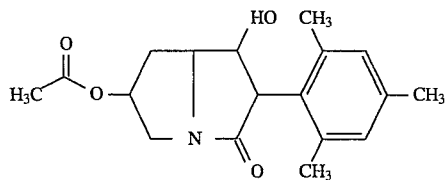

13.67 g (50 mmol) of 3-(2,4,6-trimethylphenyl)-1-aza-7-hydroxy-bicyclo-(3,3,0$^{1.5}$)octane-2,4-dione are stirred for 16 hours at ambient temperature with 50 ml of a 33% solution of hydrogen bromide in glacial acetic acid. Tow ork up the reaction mixture is poured in 1 l of ice water, the precipitate is sucked off and dried at 5° C. in the vacuum drying oven. 11.9 g (76% of theory) of 3-(2,4,6-trimethylphenyl)-1-aza-7-acetyloxy-bicyclo-(3,3,0$^{1.5}$)-octane-2,4-dione having a melting point of 223°–224° C. are obtained.

EXAMPLE 6

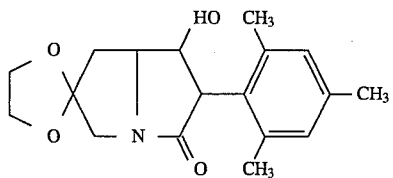

13.55 g (50 mmol) of 3-(2,4,6-trimethylphenyl)-1-aza-7-hydroxy-bicyclo-(3,3,0$^{1.5}$)-octane-2,4-dione, 15.53 g (250 mmol) of ethylene glycol and 0.5 g of p-toluene sulphonic acid are boiled in the water separator for 16 hours in 250 ml of absolute toluene. After cooling down to ambient temperature the precipitate is sucked off, washed with toluene and dried 15.24 g (86% of theory) of 3-(2,4,6-trimethylphenyl)-1-aza-7-(2,5-dioxospiropentyl)-bicyclo-(3,3,0$^{1.5}$)-octane-2.4-dione having a melting point of 235° to 236° C. are obtained.

The substituted bicyclic 3-arylpyrrolidine-2,4-dione derivatives of the formula (I)

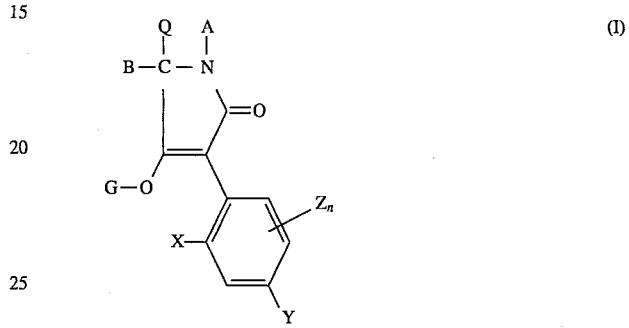

which are listed in Table 2 are obtained analogously to Preparation Examples 1 to 3 and following the general instructions in the processes according to the invention.

TABLE 2

| Ex. No. | A Q | B | X | Y | $Z_n$ | G | Physical data |
|---|---|---|---|---|---|---|---|
| 7 | $-CH(CH_3)-CH(CH_3)-CH_2-$ | H | $CH_3$ | $CH_3$ | 6-$CH_3$ | $-CO_2C_2H_5$ | oil |
| 8 | $-CH(CH_3)-CH(CH_3)-CH_2-$ | H | $CH_3$ | $CH_3$ | 6-$CH_3$ | $-CO_2CH(C_2H_5)CH_2-OC_2H_5$ | oil |
| 9 | $-CH(CH_3)-CH(CH_3)-CH_2-$ | H | $CH_3$ | $CH_3$ | 6-$CH_3$ | $-\underset{O}{\overset{\parallel}{C}}-C_6H_5$ | oil |
| 10 | $-CH(CH_3)-CH(CH_3)-CH_2-$ | H | $CH_3$ | $CH_3$ | 6-$CH_3$ | $-\underset{O}{\overset{\parallel}{C}}-CH_2-C_4H_{9t}$ | oil |
| 11 | $-CH(CH_3)-CH(CH_3)-CH_2-$ | H | $CH_3$ | $CH_3$ | 6-$CH_3$ | $-\underset{O}{\overset{\parallel}{C}}-CH=C(CH_3)_2$ | oil |
| 12 | $-CH(CH_3)-CH_2-CH(CH_3)-$ | H | $CH_3$ | $CH_3$ | 6-$CH_3$ | H | 216–217° C. |
| 13 | $-CH(CH_3)-CH_2-CH(CH_3)-$ | H | $CH_3$ | $CH_3$ | 6-$CH_3$ | $-\underset{O}{\overset{\parallel}{C}}-CH_3$ | 115–116° C. |
| 14 | $-CH(CH_3)-CH_2-CH(CH_3)-$ | H | $CH_3$ | $CH_3$ | 6-$CH_3$ | $-\underset{O}{\overset{\parallel}{C}}-C_4H_{9t}$ | 90–91° C. |
| 15 | $-CH(CH_3)-CH_2-CH(CH_3)-$ | H | $CH_3$ | $CH_3$ | 6-$CH_3$ | $-CO_2C_2H_5$ | 67–88° C. |
| 16 | $-CH(C_2H_5)-CH(CH_3)-CH_2-$ | H | $CH_3$ | $CH_3$ | 6-$CH_3$ | H | 244–246° C. |
| 17 | $-CH(C_2H_5)-CH(CH_3)-CH_2-$ | H | $CH_3$ | $CH_3$ | 6-$CH_3$ | $-\underset{O}{\overset{\parallel}{C}}-CH_3$ | |
| 18 | $-CH(C_2H_5)-CH(CH_3)-CH_2-$ | H | $CH_3$ | $CH_3$ | 6-$CH_3$ | $-\underset{O}{\overset{\parallel}{C}}-C_4H_{9t}$ | 80–81° C. |
| 19 | $-CH(C_2H_5)-CH(CH_3)-CH_2-$ | H | $CH_3$ | $CH_3$ | 6-$CH_3$ | $-CO_2C_2H_5$ | 92° C. |

5,585,384

TABLE 2-continued

| 20 | —CH—CH(CH$_3$)—CH$_2$—<br>　\|<br>　C$_6$H$_5$ | H | CH$_3$ | CH$_3$ | 6-CH$_3$ | H | 192–193° C. |
| 21 | —CH—CH(CH$_3$)—CH$_2$—<br>　\|<br>　C$_6$H$_5$ | H | CH$_3$ | CH$_3$ | 6-CH$_3$ | —C(=O)—CH$_3$ | 56–57° C. |
| 22 | —CH—CH(CH$_3$)—CH$_2$—<br>　\|<br>　C$_6$H$_5$ | H | CH$_3$ | CH$_3$ | 6-CH$_3$ | —C(=O)—C$_4$H$_{9t}$ | 133–134° C. |
| 23 | —CH$_2$—CH(OH)—CH$_2$— | H | CH$_3$ | CH$_3$ | 6-CH$_3$ | H | from 100° C. decomp. |
| 24 | —CH(CH$_3$)—CH(CH$_3$)—CH$_2$— | H | CH$_3$ | CH$_3$ | 6-CH$_3$ | —COC(CH$_3$)$_2$C$_2$H$_5$ | oil |
| 25 | —CH(CH$_3$)—CH(CH$_3$)—CH$_2$— | H | Cl | Cl | H | H | 185–194° C. |
| 26 | —CH(CH$_3$)—CH(CH$_3$)—CH$_2$— | H | CH$_3$ | CH$_3$ | 6-CH$_3$ | —P(=S)(CH$_3$)—SC$_4$H$_9$ | |
| 27 | —CH(CH$_3$)—CH(CH$_3$)—CH$_2$ | H | CH$_3$ | CH$_3$ | 6-CH$_3$ | —P(=S)(CH$_3$)—C$_4$H$_{9i}$ | |
| 28 | —CH(CH$_3$)—CH(CH$_3$)—CH$_2$ | H | Cl | Cl | H | —C(=O)—C(CH$_3$)$_3$ | 99–101° C. |
| 29 | —CH(CH$_3$)—CH(CH$_3$)—CH$_2$ | H | Cl | Cl | H | —C(=O)—C(CH$_3$)$_3$(C$_2$H$_5$) | |
| 30 | —CH(CH$_3$)—CH(CH$_3$)—CH$_2$— | H | Cl | Cl | H | —C(=O)—OC$_4$H$_{9sec}$ | 64–70° C. |
| 31 | —CH(CH$_3$)—CH(CH$_3$)—CH$_2$— | H | Cl | Cl | H | —C(=O)—OC$_4$H$_{9iso}$ | 97–99° C. |
| 32 | —CH(CH$_3$)—CH(CH$_3$)—CH$_2$— | H | Cl | Cl | H | —C(=O)—C(CH$_3$)$_3$ | 141–142° C. |
| 33 | —CH(CH$_3$)—CH(CH$_3$)—CH$_2$— | H | Cl | Cl | H | —C(=O)—C(CH$_2$)$_2$—C$_2$H$_5$ | 94–104° C. |
| 34 | —CH(CH$_3$)—CH(CH$_3$)—CH$_2$— | H | Cl | Cl | H | —C(=O)—OC$_4$H$_{9sec}$ | 84–86° C. |
| 35 | —CH(CH$_3$)—CH(CH$_3$)—CH$_2$— | H | CH$_3$ | CH$_3$ | 6-CH$_3$ | —C(=O)—C(CH$_3$)$_2$C$_3$H$_{7i}$ | oil |
| 36 | —CH(CH$_3$)—CH(CH$_3$)—CH$_2$— | H | CH$_3$ | CH$_3$ | 6-CH$_3$ | —C(=O)—OC$_4$H$_{9s}$ | oil |
| 37 | —CH(CH$_3$)—CH(CH$_3$)—CH$_2$— | H | CH$_3$ | CH$_3$ | 6-CH$_3$ | —C(=O)—OC$_4$H$_{9i}$ | oil |
| 38 | —CH(CH$_3$)—CH(CH$_3$)—CH$_2$— | H | CH$_3$ | CH$_3$ | 6-CH$_3$ | —C(=O)—S(CH$_2$)$_2$—C$_4$H$_{9t}$ | oil |

TABLE 2-continued

| # | | | | | | | |
|---|---|---|---|---|---|---|---|
| 39 | —CH(CH$_3$)—CH(CH$_3$)—CH(CH$_3$)— | H | CH$_3$ | CH$_3$ | 6-CH$_3$ | —C(=O)—C(CH$_2$)$_2$C$_3$H$_{7i}$ | 97–99° C. |
| 40 | —CH(CH$_3$)—CH(CH$_3$)—CH(CH$_3$)— | H | CH$_3$ | CH$_3$ | 6-CH$_3$ | —C(=O)—CH$_2$—C$_4$H$_{9t}$ | oil |
| 41 | —CH(CH$_3$)—CH(CH$_3$)—CH(CH$_3$)— | H | CH$_3$ | CH$_3$ | 6-CH$_3$ | —C(=O)—OC$_4$H$_{9i}$ | oil |
| 42 | —CH(CH$_3$)—CH(CH$_3$)—CH(CH$_3$)— | H | CH$_3$ | CH$_3$ | 6-CH$_3$ | —C(=O)—OC$_4$H$_{9s}$ | oil |
| 43 | —CH(CH$_3$)—CH(CH$_3$)—CH(CH$_3$)— | H | CH$_3$ | CH$_3$ | 6-CH$_3$ | —C(=O)—OCH$_2$—CH(C$_2$H$_5$)—C$_4$H$_9$ | oil |
| 44 | —CH(CH$_3$)—CH(CH$_3$)—CH(CH$_3$)— | H | CH$_3$ | CH$_3$ | 6-CH$_3$ | —C(=O)—SCH$_2$—C$_4$H$_{9t}$ | 105–110° C. |
| 45 | —CH(CH$_3$)—CH$_2$—CH(CH$_3$)— | H | CH$_3$ | CH$_3$ | 6-CH$_3$ | —SO$_2$CH$_3$ | oil |
| 46 | —CH$_2$\\CH(—O—C(=O)—CH$_3$)/—CH$_2$— | H | CH$_3$ | CH$_3$ | 6-CH$_3$ | —C(=O)—CH$_3$ | oil |
| 47 | —CH$_2$\\CH(—O—C(=O)—C$_4$H$_{9t}$)/—CH$_2$— | H | CH$_3$ | CH$_3$ | 6-CH$_3$ | —C(=O)—C$_4$H$_{9t}$ | oil |
| 48 | —CH$_2$\\CH(—O—C(=O)—CH$_3$)/—CH$_2$— | H | CH$_3$ | CH$_3$ | 6-CH$_3$ | —C(=O)—CH$_2$C$_4$H$_{9t}$ | oil |
| 49 | —CH$_2$\\CH(—O—C(=O)—CH$_3$)/—CH$_2$— | H | CH$_3$ | CH$_3$ | 6-CH$_3$ | —C(=O)—OC$_4$H$_{9s}$ | oil |
| 50 | —CH$_2$—C(=O)—CH$_2$— | H | CH$_3$ | CH$_3$ | 6-CH$_3$ | —C(=O)—CH$_3$ | 60–61° C. |
| 51 | —CH$_2$—C(=O)—CH$_2$— | H | CH$_3$ | CH$_3$ | 6-CH$_3$ | —C(=O)—C$_4$H$_{9t}$ | 126–128° C. |
| 52 | —CH$_2$—C(=O)—CH$_2$— | H | CH$_3$ | CH$_3$ | 6-CH$_3$ | —C(=O)—OC$_4$H$_{9i}$ | oil |
| 53 | —CH$_2$—C(=O)—CH$_2$— | H | CH$_3$ | CH$_3$ | 6-CH$_3$ | —C(=O)—C$_6$H$_5$ | 148–149° C. |
| 54 | [—O—CH$_2$\\C/—O—CH$_2$—] | H | CH$_3$ | CH$_3$ | 6-CH$_3$ | —C(=O)—CH$_3$ | 125–126° C. |
| 55 | [—O—CH$_2$\\C/—O—CH$_2$—] | H | CH$_3$ | CH$_3$ | 6-CH$_3$ | —C(=O)—C$_4$H$_{9t}$ | 140–141° C. |

TABLE 2-continued

| Ex. No. | A Q | B | X | Y | $Z_n$ | G | Fp[°C.] |
|---|---|---|---|---|---|---|---|
| 56 | $\begin{array}{c}\text{O}-\text{CH}_2-\\ \diagup\diagdown\\ \text{C}\\ \diagup\diagdown\\ \text{O}-\text{CH}_2-\end{array}$ | H | CH$_3$ | CH$_3$ | 6-CH$_3$ | $-\underset{\underset{O}{\parallel}}{C}-C(CH_3)_2C_3H_{7i}$ | oil |
| 57 | (same dioxa ring) | H | CH$_3$ | CH$_3$ | 6-CH$_3$ | $-\underset{\underset{O}{\parallel}}{C}-OCH_2-\underset{\underset{C_2H_5}{\mid}}{CH}-C_4H_9$ | oil |
| 58 | (propylene dioxa ring) | H | CH$_3$ | CH$_3$ | 6-CH$_3$ | H | 172–173° C. |
| 59 | (propylene dioxa ring) | H | CH$_3$ | CH$_3$ | 6-CH$_3$ | $-\underset{\underset{O}{\parallel}}{C}-CH_3$ | oil |
| 60 | (propylene dioxa ring) | H | CH$_3$ | CH$_3$ | 6-CH$_3$ | $-\underset{\underset{O}{\parallel}}{C}-C(CH_3)_2C_3H_{7i}$ | oil |
| 61 | (propylene dioxa ring) | H | CH$_3$ | CH$_3$ | 6-CH$_3$ | $-\underset{\underset{O}{\parallel}}{C}-OCH_2-\underset{\underset{C_2H_5}{\mid}}{CH}-C_4H_9$ | oil |
| 62 | $\begin{array}{c}\text{CH}_3\\ \diagdown\\ \text{C}(\text{CH}_3)_2\text{ dioxa ring}\end{array}$ | H | CH$_3$ | CH$_3$ | 6-CH$_3$ | H | 254–256° C. |
| 63 | (dimethyl dioxa ring) | H | CH$_3$ | CH$_3$ | 6-CH$_3$ | $-\underset{\underset{O}{\parallel}}{C}-CH_3$ | oil |
| 64 | (dimethyl dioxa ring) | H | CH$_3$ | CH$_3$ | 6-CH$_3$ | $-\underset{\underset{O}{\parallel}}{C}-\underset{\underset{C_3H_7}{\mid}}{C}(CH_3)_2$ | oil |
| 65 | (dimethyl dioxa ring) | H | CH$_3$ | CH$_3$ | 6-CH$_3$ | $-\underset{\underset{O}{\parallel}}{C}-OCH_2-\underset{\underset{C_2H_5}{\mid}}{CH}-C_4H_9$ | oil |
| 66 | —(CH$_2$)$_3$CH(CH$_3$)— | H | CH$_3$ | CH$_3$ | 6-CH$_3$ | H | 240–243 |
| 67 | —(CH$_2$)$_3$CH(CH$_3$)— | H | CH$_3$ | CH$_3$ | 6-CH$_3$ | COCH$_3$ | oil |
| 68 | —(CH$_2$)$_3$CH(CH$_3$)— | H | CH$_3$ | CH$_3$ | 6-CH$_3$ | COC(CH$_3$)$_3$ | 88–91 |
| 69 | —(CH$_2$)$_3$CH(CH$_3$)— | H | CH$_3$ | CH$_3$ | 6-CH$_3$ | CO$_2$CH$_2$CH(CH$_3$)$_2$ | oil |
| 70 | —(CH$_2$)$_3$CH(CH$_3$)— | H | CH$_3$ | CH$_3$ | 6-CH$_3$ | CO$_2$CH(CH$_3$)CH$_2$CH$_3$ | oil |

Preparation of the intermediates

Example (II-1)

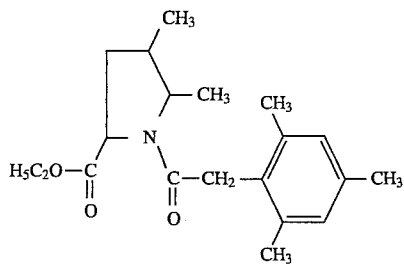

11.7 g (0.068 mol) of ethyl 4,5-dimethyl-pyrrolidine-2-carboxylate and 9.6 ml of triethylamine are cooled to from 0° C. to 10° C., and 13.4 g (0.068 mol) of mesityleneacetyl chloride in 10 ml of absolute tetrahydrofuran are added dropwise to this mixture. The batch is subsequently stirred at room temperature until the reaction has ended (TLC monitoring). The reaction mixture is then stirred into a solution of 300 ml of ice-water and 100 ml of 1N hydrochloric acid, extracted with dichloromethane and dried, and the solvent is stripped off under reduced pressure.

16 g (71% of theory) of ethyl N-(2,4,6-trimethylphenylacetyl-4,5-dimethyl-pyrrolidine-2-carboxylate are obtained as an oil.

Example (II-2)

Methyl N-(2,4,6-trimethylphenylacetyl-4-hydroxy-pyrrolidine-2-carboxylate of melting point 138°–139° C. is obtained analogously to Example (II-1).

Use Examples:

In the following Use Examples, the compounds listed below were employed as comparison substances:

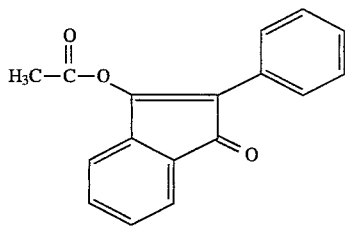

3-(acetyloxy)-2-phenyl-1H-inden-1-one (disclosed in U.S. Pat. No. 4,104,043)

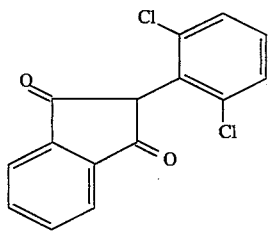

2-(2,6-dichlorophenyl)-1H-indene-1,3(2H)-dione (disclosed in U.S. Pat. No. 3,954,998)

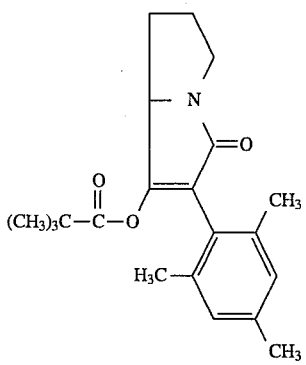

2,2-dimethyl-2,3,5,7a-tetrahydro-5-oxo-6-(2,4,6-trimethylphenyl)-1H-pyrrolizin-7-yl-propionic acid ester (disclosed in EP-A 355,599)

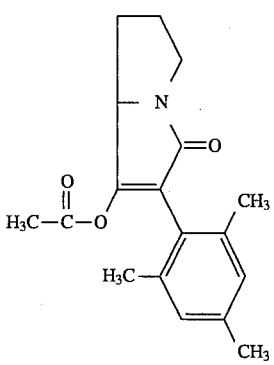

1-(acetyloxy)-5,6,7,7a-tetrahydro-2-(2,4,6-trimethylphenyl)-3H-pyrrolizin-3-one (disclosed in EP-A 355,599)

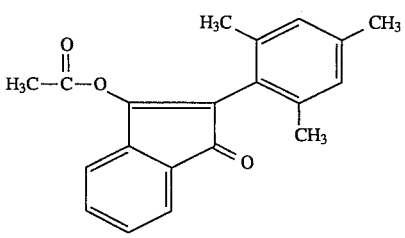

3-(acetyloxy)-2-(2,4,6-trimethylphenyl)-1H-inden-1-one (disclosed in U.S. Pat. No. 4,104,043)

Example A

Nephotettix test

Solvent: 7 parts by weight of dimethylformamide

Emulsifier: 1 part by weight of alkylaryl polyglycol ether

To produce a suitable preparation of active compound, 1 part by weight of the active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the green rice cicada (*Nephotettix cincticeps*) while the seedlings are still moist.

After the desired period of time, the destruction in percent is determined. 100% means that all cicadas have been killed; 0% means that none of the cicadas have been killed.

In this test, a superior activity compared with the prior art is shown, for example, by the following compounds of the Preparation Examples: 1, 2 and 3.

Example B

Phaedon larvae test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, a superior activity compared with the prior art is shown, for example, by the following compounds of the Preparation Examples: 1, 2 and 3.

Example C

Tetranychus test (OP resistant)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the greenhouse red spider mite or two-spotted spider mite (*Tetranychus urticae*) are treated by being dipped into the active compound preparation of the desired concentration.

After the specified period of time, the destruction in percent is determined. 100% means that all spider mites have been killed; 0% means that none of the spider mites have been killed.

In this test, a superior activity compared with the prior art is shown, for example, by the following compounds of the Preparation Examples: 2 and 3.

Example D

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development Of the untreated control. The figures denote:

0%=no action (like untreated control)

100%=total destruction

Compared with the prior art, a clearly superior activity and crop plant selectivity is shown, in this test, for example by the compounds in accordance with Preparation Examples 1, 2 and 3.

Example E

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0%=no action (like untreated control)

100%=total destruction

Compared with the prior art, a clearly superior activity and crop plant selectivity is shown, in this test, for example by the compound in accordance with Preparation Example 1.

We claim:

1. A bicyclic 3-aryl-pyrrolidine-2 one derivatives of the formula

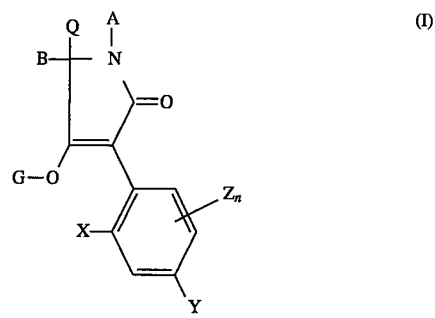

wherein

A and Q together represent an alkanediyl, group having 4 carbon atoms monosubstituted to trisubstituted by alkyl having 1 to 6 carbon atoms;

B represents hydrogen, methyl or ethyl,

X represents methyl, ethyl, propyl or 2-propyl,

Y represents methyl, ethyl, propyl, or i-propyl,

Z represents methyl, ethyl, propyl, or i-propyl, n represents a number 0, 1, 2 or 3, G represents hydrogen (a) or the groups —CO—$R^1$ (b), or

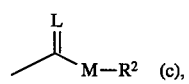

in which

L and M in each case represent oxygen and/or sulphur, $R^1$ represents optionally fluorine- or chlorine-substituted $C_1$–$C_{14}$-alkyl, $C_2$–$C_{14}$-alkenyl, $C_1$–$C_4$-alkoxy-$C_2$–$C_6$- alkyl, $C_1$–$C_4$-alkylthio-$C_2$–$C_6$-alkyl, $C_1$–$C_4$-polyalkoxy-$C_2$–$C_4$-alkyl or cycloalkyl which has 3 to 6 ring atoms and which can be interrupted by 1 to 2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy or nitro-, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy-, or represents pyridyl, pyrimidyl, thiazolyl and pyrazolyl which are optionally substituted by fluorine, chlorine, bromine, methyl or ethyl-, or represents phenoxy-$C_1$–$C_4$-alkyl which is optionally substituted by fluorine, chlorine, methyl or ethyl-, or represents pyridyloxy-$C_1$–$C_4$-alkyl, pyrimidyloxy-$C_1$–$C_4$-alkyl and thiazolyloxy-$C_1$–$C_4$-alkyl which are optionally substituted by fluorine, chlorine, amino, methyl- or ethyl, $R^2$ represents $C_1$–$C_{14}$-alkyl, $C_2$–$C_{14}$-alkenyl, $C_1$–$C_4$-alkoxy-$C_2$–$C_6$-alkyl or $C_1$–$C_4$-polyalkoxy-$C_2$–$C_6$-alkyl which are optionally substituted by fluorine or chlorine, or represents phenyl or benzyl which are optionally substituted by fluorine, chlorine, nitro, methyl, ethyl, propyl, i-propyl, methoxy, ethoxy, trifluoromethyl.

2. Substituted bicyclic 3-aryl-pyrrolidone-2,4-dione derivatives of the formula (I) according to claim 1, characterized that A and Q together represent an alkanediyl group having 4 carbon atoms monosubstituted by methyl, B is hydrogen, and $Z_n$ is 6-methyl.

3. An insecticidal or acaricidal composition comprising an amount effective therefor of a compound according to claim 1, and a diluent.

4. A method of combatting insects or acarids which comprises applying thereto or to a locus from which it is desired they be excluded an amount effective therefor of a compound according to claim 1, and a diluent.

5. A herbicidal composition comprising an amount effective therefor of a compound according to claim 1 and a diluent.

6. A method of combatting unwanted vegetation which comprises applying thereto or to a locus from which it is desired they be excluded an amount effective therefor of a compound according to claim 1 and a diluent.

7. A compound according to claim 1, wherein $R^1$ represents optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl, $C_1$–$C_4$-alkylthio-$C_2$–$C_6$-alkyl, $C_1$–$C_4$-polyalkoxy-$C_2$–$C_4$-alkyl or cycloalkyl which has 3 to 6 ring atoms or represents phenyl which is optionally substituted by fluorine, chlorine, bromine, methyl, ethyl, propyl, i-propyl, methoxy, ethoxy, trifluoromethyl, trifluoromethoxy or nitro-, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy-, or represents phenoxy-$C_1$–$C_4$-alkyl which is optionally substituted by fluorine, chlorine, methyl or ethyl-, $R^2$ represents $C_1$–$C_{14}$-alkyl, $C_2$–$C_{14}$-alkenyl, $C_1$–$C_4$-alkoxy-$C_2$–$C_6$-alkyl or $C_1$–$C_4$-polyalkoxy-$C_2$–$C_6$-alkyl which are optionally substituted by fluorine or chlorine, or represents phenyl or benzyl which are optionally substituted by fluorine, chlorine, nitro, methyl, ethyl, propyl, i-propyl, methoxy, ethoxy, trifluoromethyl.

8. A compound according to claim 1, wherein G is hydrogen.

9. The compound according to claim 1, wherein the compound is

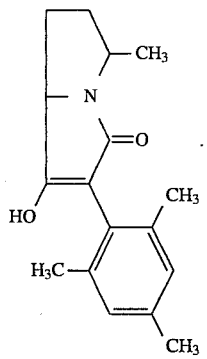

* * * * *

UNITED STATES PATENT AND TRADEMARK OFFICE
CERTIFICATE OF CORRECTION

PATENT NO. : 5,585,384
DATED      : December 17, 1996
INVENTOR(S) : Santel, et al.

It is certified that error appears in the above-indentified patent and that said Letters Patent is hereby corrected as shown below:

Col. 66, last line   Delete " 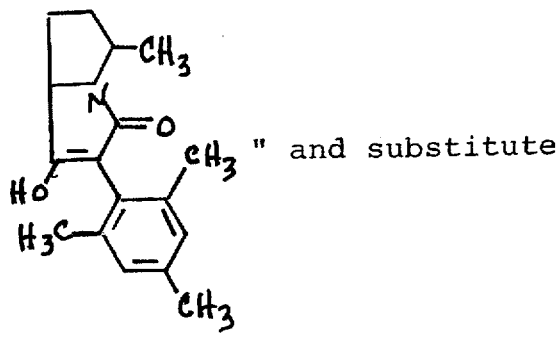 " and substitute

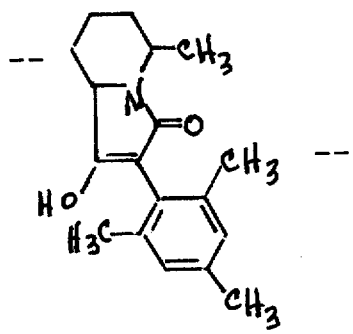

--

Signed and Sealed this

Tenth Day of June, 1997

Attest:

Attesting Officer

BRUCE LEHMAN

Commissioner of Patents and Trademarks